(12) United States Patent
Noda et al.

(10) Patent No.: US 9,816,113 B2
(45) Date of Patent: Nov. 14, 2017

(54) METHOD FOR PRODUCING ETHANOL

(71) Applicants: Kansai Chemical Engineering Co., Ltd., Hyogo (JP); Bio-energy Corporation, Hyogo (JP)

(72) Inventors: Hideo Noda, Hyogo (JP); Shinji Hama, Hyogo (JP); Kohsuke Nakano, Hyogo (JP)

(73) Assignees: Kansai Chemical Engineering Co., Ltd., Hyogo (JP); Bio-Energy Corporation, Hyogo (JP)

( * ) Notice: Subject to any disclaimer, the term of this patent is extended or adjusted under 35 U.S.C. 154(b) by 0 days.

(21) Appl. No.: 14/915,948

(22) PCT Filed: Sep. 3, 2014

(86) PCT No.: PCT/JP2014/073149
§ 371 (c)(1),
(2) Date: Mar. 2, 2016

(87) PCT Pub. No.: WO2015/033948
PCT Pub. Date: Mar. 12, 2015

(65) Prior Publication Data
US 2016/0201092 A1    Jul. 14, 2016

(30) Foreign Application Priority Data
Sep. 4, 2013  (JP) ................. 2013-183082

(51) Int. Cl.
| C12P 7/10 | (2006.01) |
| C12P 7/06 | (2006.01) |
| C12N 9/00 | (2006.01) |
| C12N 9/14 | (2006.01) |
| C12N 9/16 | (2006.01) |
| C12N 9/24 | (2006.01) |
| C12N 9/26 | (2006.01) |
| C12N 9/34 | (2006.01) |
| C12N 9/38 | (2006.01) |
| C12N 9/44 | (2006.01) |
| C12N 9/46 | (2006.01) |
| C12N 1/00 | (2006.01) |

(52) U.S. Cl.
CPC ............. *C12P 7/10* (2013.01); *Y02E 50/16* (2013.01)

(58) Field of Classification Search
CPC .................... Y02E 50/16; C12P 7/10
USPC ....... 435/165, 161, 183, 195, 196, 200, 201, 435/205, 207, 210, 211, 254.11
See application file for complete search history.

(56) References Cited

U.S. PATENT DOCUMENTS 7,192,764 B2   3/2007   Fukuda et al.

8,574,911 B2     11/2013   Noda et al.
2012/0282666 A1  11/2012   Noda et al.

FOREIGN PATENT DOCUMENTS

| JP | 11-290078      |   | 10/1999 |          |
|----|----------------|---|---------|----------|
| JP | 2011-142879    |   | 7/2011  |          |
| JP | 2011-254748    |   | 12/2011 |          |
| JP | 2012-139211    |   | 7/2012  |          |
| JP | 2012139211MT   | * | 7/2012  | ......... C12P 7/08 |
| JP | 2013-135641    |   | 7/2013  |          |
| WO | 02/085935 A1   |   | 10/2002 |          |
| WO | 03/016525 A1   |   | 2/2003  |          |
| WO | 2010/032762 A1 |   | 3/2010  |          |
| WO | 2010/098408 A1 |   | 9/2010  |          |
| WO | 2011/067960 A1 |   | 6/2011  |          |
| WO | 2014/157141 A1 |   | 10/2014 |          |

OTHER PUBLICATIONS

Chundawat et al., Effect of particle size based on separation of milled corn stover on APEX pretreatment and enzymatic digestability. Biotechnol. Bioeng., 2007, vol. 96 (2): 219-231.*
Katahira et al., Construction of a xylan-fermenting yeast strain through codisplay of xylanolytic enzymes on the surface of xylose-utilizing *Saccharomyces cerevisiae* cells. Appl. Environ. Microbiol., 2004, vol. 70 (9); 5407-5414.*
Shinichi Yano, "Focused on Cellulases and Hemicellulases", Research Frontier of Biomass Degrading Enzymes Chapter 24: Enzymatic Degradation of Mechanically Pretreated Biomass, CMC Publishing Co., Ltd., 1st edition, 2012.
Arata Itoh et al, "Study of Mechanical Pulverization Technique for Bioethanol Production (II) (Large-Capacity Test of Vibrating Mill Using Gear-Type Pulverizing Medium)" Proceedings of Spring Conference in 2007 (Tokyo) of the Mining and Materials Processing Institute of Japan.
Yukio Enda et al., "Simultaneous Saccharification and Fermentation Characteristic of Biomass Pulverized with High Impact", 77th Annual Meeting of the Society of Chemical Engineers, Japan 2012.
Yuki Matano et al., "Display of cellulases on the cell surface of *Saccharomyces cerevisiae* for high yield ethanol production from high-solid lignocellulosic biomass", Bioresource Technology, vol. 108, pp. 128-133 (2012).
Churairat Moukamnerd et al, "Ethanol production from biomass by repetitive solid-state fed-batch fermentation with continuous recovery of ethanol", Appl Microbiol Biotechnol vol. 88, pp. 87-94 (2010).
Yueqin Tang et al., "Ethanol production from acid hydrolysate of wood biomass using the flocculating yeast *Saccharomyces cerevisiae* strain KF-7", Process Biochemistry, vol. 41, pp. 909-914 (2006).

(Continued)

*Primary Examiner* — Ganapathirama Raghu
(74) *Attorney, Agent, or Firm* — Ajay A. Jagtiani; Miles & Stockbridge P.C.

(57) ABSTRACT

Disclosed is a method for producing ethanol, including: culturing yeast transformed so as to display an enzyme on the cell surface in a medium containing particles of lignocellulosic biomass, thereby producing ethanol, wherein the enzyme is an enzyme involved in hydrolysis of the lignocellulosic biomass. The present invention makes it possible to provide a method for producing ethanol by which a high ethanol yield can be achieved from lignocellulosic biomass with lower initial cell concentration and added enzyme amount.

6 Claims, 12 Drawing Sheets

(56) References Cited

OTHER PUBLICATIONS

Hiroshi Kitagaki et al., "Identification and analysis of a static culture-specific cell wall protein, Tir1p/Srp1p in *Saccharomyces cerevisiae*", Eur. J. Biochem., vol. 249, pp. 343-349 (1997).

Satoshi Katahira et al., "Ethanol fermentation from lignocellulosic hydrolysate by a recombinant xylose- and cellooligosaccharide-assimilating yeast strain", Appl Microbial Biotechnol, vol. 72, pp. 1136-1143 (2006).

Toshiyuki Murai et al., "Construction of a Starch-Utilizing Yeast by Cell Surface Engineering", Applied and Environmental Microbiology, vol. 63, No. 4, pp. 1362-1366 (1997).

Ryosuke Yamada et al., "Efficient production of ethanol from raw starch by a mated diploid *Saccharomyces cerevisiae* with integrated aamylase and glucoamylase genes" Enzyme and Microbial Technology, vol. 44, pp. 344-349 (2009).

Tsuyoshi Suzuki et al., "Composition of Tricoderma reesei Cellulase suitable for Enzymatic Saccharification of Pulverized Cedar Wood (Bifunsai Sugi no Koso Toka ni Saiteki na Tricoderma reesei Cellulase no Sosei)", Japan Society for Bioscience, Biotechnology, and Agrochemistry Taikai Koen Yoshishu, vol. 2010, 3XCa02, p. 253 (2010).

Hirokazu Murayama et al., "Improvement of fermentation on soft-biomass with yeast displaying enzyme derived from *Aspergillus oryzae*", Japan Society for Bioscience, Biotechnology,and Agrochemistry Nenji Taikai Koen Happyo Database(Online), 2C12p08 (Mar. 25, 2013).

Hiromoto Hisada et al., "Kojikin Yurai Ferulic Acid Esterase o Mochiita Soft Biomass no Toka Koritsu Kaizen", Japan Society for Bioscience, Biotechnology, and Agrochemistry Taikai Koen Yoshishu, vol. 2010, 3XCp13, p. 256 (2010).

Yukio Enda et al., Slides of "Review on Cost Reduction for Bioethanol Production Process from of Akita Ceder Pulverized with High Impact", The 23rd Annual Conference of Japan Society of Material Cycles and Waste Management, B13-3, Oct. 24, 2012.

Miki Ota, "Display of Clostridium cellulovorans Xylose Isomerase on the Cell Surface of Saccharomyces and its Direct Application to Xylose Fermentation", Biotechnol. Prog., vol. 29, No. 2 (2013).

M.G. Tabka et al., "Enzymatic saccharification to wheat straw for bioethanol production by a combined cellulase xylanase and feruloyl esterase treatement", Enzyme and Microbial Technology, vol. 39, pp. 897902 (2006).

International Preliminary Report on Patentability and Written Opinion received in PCT Application No. PCT/JP2014/073149 dated Mar. 8, 2016.

* cited by examiner (a)

(b)

(a)

(b)

(c)

(d)

(e)

(a)

(b)

(a)

(b)

(c)

METHOD FOR PRODUCING ETHANOL

TECHNICAL FIELD

The present invention relates to a method for producing ethanol, and more specifically relates to a method for producing ethanol through fermentation by yeast from finely pulverized lignocellulosic biomass.

BACKGROUND ART

Techniques for producing ethanol from lignocellulosic biomass, which does not compete with food, have been extensively developed. Lignocellulosic biomass may be degraded typically by treatment with saccharifying enzymes (e.g., cellulase) for fermentation by yeast.

The main components of lignocellulosic biomass are cellulose, hemicellulose, and lignin. Cellulose in the biomass has a rigid crystalline structure. In order to enzymatically degrade the lignocellulosic biomass, it is always necessary to pretreat the biomass to be easily in contact with and reacted with the enzyme.

As the pretreatment for the lignocellulosic biomass, methods using various principles have been proposed, which are genetically classified into physical treatment, chemical treatment, and biological treatment.

Examples of the physical treatment include finely pulverizing treatment. The finely pulverizing treatment is a method for finely pulverizing lignocellulosic biomass using a mill or the like. Enzymatic degradation (saccharification) is enhanced by the finely pulverizing treatment, for example, because increased contact area of biomass with enzymes by reduced particle size of biomass, decreased crystallinity and polymerization for cellulose, and the separation of cellulose molecules in units of microfibrils (Non-Patent Document 1).

Of these, methods for causing a chemical reaction (cleavage or formation of bonds) using a mechanical energy such as pulverization are referred to as mechanochemical treatment. As a mill for high impact and energy conservation, a tandem-ring mill using the ring-type pulverizing medium tumbling method has been developed (Non-Patent Document 2). When cedarwood that was preliminarily pulverized using a ball mill and then classified into a particle size of 200 μm or less with a sieve is subjected to the tandem-ring mill, the average particle size of the cedarwood reaches about 20 μm in 10 to 20 minutes, and when the pulverization is continued up to 60 minutes, the saccharification rate can be maximum. An example has been reported in which finely pulverized cedarwood obtained in the tandem-ring mill is saccharified with a commercially available cellulase preparation and is then fermented by yeast, so that ethanol is produced (Non-Patent Document 3).

Meanwhile, it has been shown that application of techniques for expressing various enzymes involved in saccharification of lignocellulose on the cell surface of microorganisms realizes a high ethanol yield from lignocellulosic biomass even with a relatively small amount of enzyme added. Non-Patent Document 4 has reported that, in ethanol production from hydrothermally treated rice straw, recombinant yeast *Saccharomyces cerevisiae* expressing three types of enzymes consisting of endoglucanase, cellobiohydrolase, and β-glucosidase on the cell surface degrades a cellulose moiety that fail to be degraded with a commercially available cellulase preparation alone, thereby exhibiting an ethanol yield higher than that of wild-type yeast.

However, in order to produce ethanol from lignocellulosic biomass, it is an important issue to reduce the use amount of enzyme necessary for saccharification, while maintaining or improving the saccharification efficiency of the enzyme. Even in the case where finely pulverized lignocellulosic biomass is used, if the use amount of enzyme is small, the saccharification and the fermentation yields may be significantly poor, and the process of recovering the enzyme from slurry after the fermentation may be complicated.

Furthermore, in order to increase the ethanol yield, it is necessary to increase the cellulase activity on the cell surface by expressing many types of enzymes at a high level. Furthermore, in order to allow the cellulase activity of the yeast on the cell surface to significantly act on increase in ethanol yield, a very high initial cell concentration is necessary. Such a high cell concentration leads to an increase in the ethanol production cost.

PRIOR ART DOCUMENTS

Non-Patent Documents

Non-Patent Document 1: Research Frontier of Biomass Degrading Enzymes—Focused on Cellulases and Hemicellulases—, Chapter 24: Enzymatic Degradation of Mechanically Pretreated Biomass, CMC Publishing Co., Ltd., 1st edition, 2012.

Non-Patent Document 2: Proceedings of Spring Conference in 2007 (Tokyo) of the Mining and Materials Processing Institute of Japan, Arata Itoh et al., Study of Mechanical Pulverization Technique for Bioethanol Production (II) (Large-Capacity Test of Vibrating Mill Using Gear-Type Pulverizing Medium).

Non-Patent Document 3: 77th Annual Meeting of the Society of Chemical Engineers, Japan, Yukio Enda et al., Simultaneous Saccharification and Fermentation Characteristic of Biomass Pulverized with High Impact, Non-Patent Document 4: Y. Matano et al., Bioresource Technology, 2012, Vol. 108, p. 128-133.

SUMMARY OF INVENTION

Problems to be Solved by the Invention

It is an object of the present invention to provide a method for producing ethanol by which a high ethanol yield can be achieved from lignocellulosic biomass with a lower initial cell concentration and a smaller amount of enzyme added.

Means for Solving the Problems

The present invention provides a method for producing ethanol, including:
culturing yeast transformed so as to display an enzyme on the cell surface in a medium containing particles of lignocellulosic biomass, thereby producing ethanol,
wherein the enzyme is an enzyme involved in hydrolysis of the lignocellulosic biomass.

In one embodiment, the particles of the lignocellulosic biomass have an average particle size of 2 μm to 600 μm.

In one embodiment, the lignocellulosic biomass further contains starch.

In one embodiment, the enzyme involved in hydrolysis of the lignocellulosic biomass is at least one enzyme selected from the group consisting of endoglucanase, cellobiohydrolase, β-glucosidase, ferulic acid esterase, β-galactosidase, pectinase, xylanase, xylosidase, acetylxylan esterase, arabinofuranosidase, swollenin, laccase, lignin peroxidase, glucoamylase, α-amylase, β-amylase, and pullulanase.

In one embodiment, the transformed yeast displays the enzyme on the cell surface so that a substrate-binding domain of the enzyme is oriented outward from the cell.

In one embodiment, the transformed yeast has xylose metabolizing ability.

In one embodiment, the method further includes finely pulverizing the lignocellulosic biomass.

In one embodiment, the method further includes hydrothermally treating the lignocellulosic biomass.

Effects of Invention

According to the present invention, it is provided a method by which ethanol can be efficiently produced from lignocellulosic biomass under practical conditions. The method of the present invention allows for, for example, low initial yeast cell concentration and reduced added cellulase amount.

MODE FOR CARRYING OUT THE INVENTION

Lignocellulosic Biomass

Figure 1:
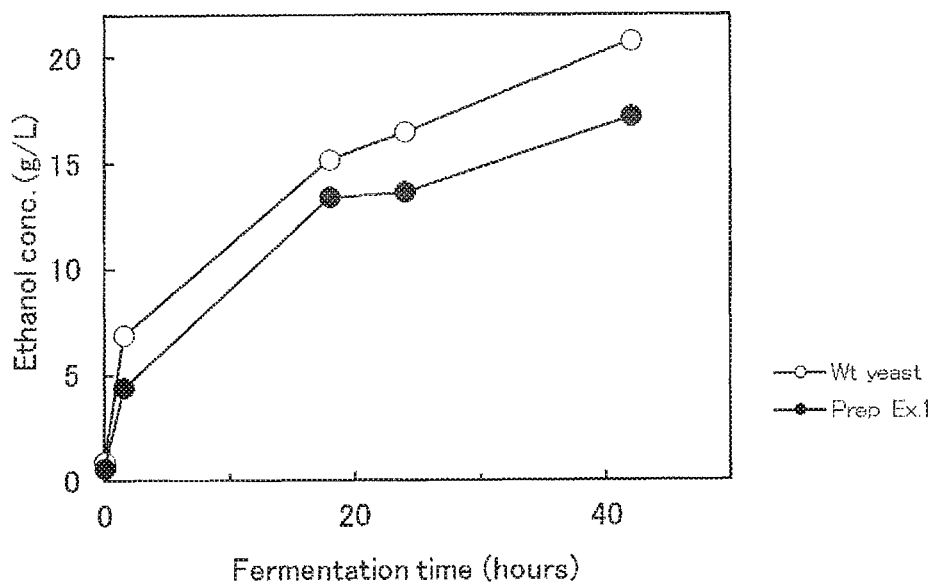
FIG. 1 shows graphs of ethanol fermentation results of hydrothermally treated rice straw (a) and finely pulverized rice straw (b) respectively, using each of wild-type yeast (NBRC1440 strain) and recombinant yeast of Preparation Example 1.
Figure 1:
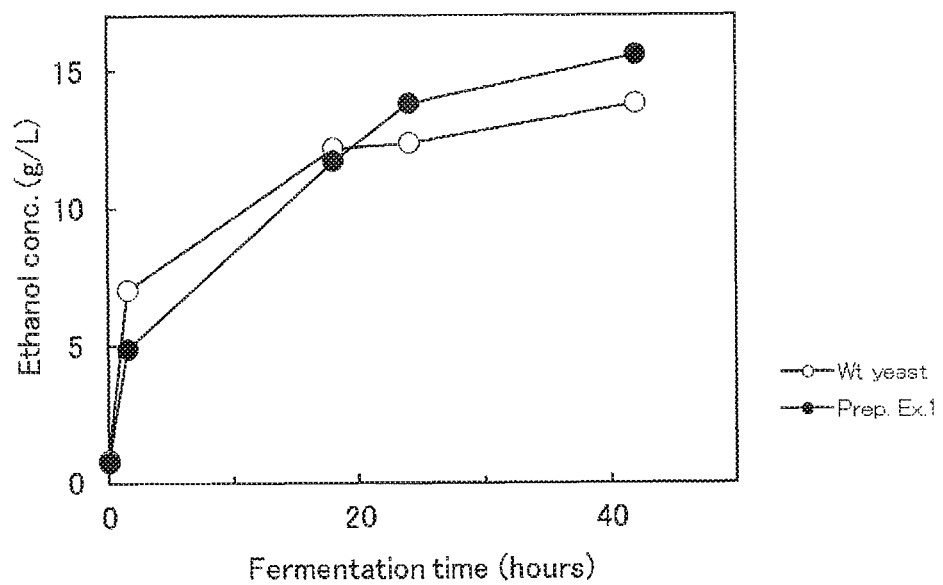

Biomass refers to a saccharine material derived from biological resources. Examples thereof include starch obtained from corn or the like and molasses (blackstrap molasses) obtained from sugarcane or the like. Lignocellulosic biomass is biomass containing so-called lignocellulose (mainly including three types of components of cellulose, hemicellulose, and lignin). Cellulose is a fibrous macromolecule in which glucopyranoses (glucoses) are polymerized by $\beta$-1,4-glucosidic bonds, and glucoses obtained by hydrolyzing cellulose are used as a fermentation substrate for yeast and the like. Although the contents of cellulose, hemicellulose, and lignin components may vary depending on the plant species (in particular, whether woody or herbaceous), the portions of such plants (organs, tissues), the extent of growth, and the like, a plant of any species in any portion at any growth stage may be used as long as glucose can be produced therefrom through enzymatic degradation.

Examples of the lignocellulosic biomass include wastes generated when treating biological materials such as rice, wheat, corn, sugarcane, wood (e.g., cedarwood, *Albizia falcataria, Chamaecyparis obtusa, Fagus crenata, Eucalyptus globulus*, etc.), bamboo, napier grass, and the like. Examples thereof include rice straw, bagasse (residue after squeezing sugarcane), timber from forest thinning, waste wood, waste grass (e.g., turf grass that may be disposed of on golf courses), and the like. The present invention can be preferably used also in the case where lignocellulosic biomass containing lignin is used as a starting material. In this manner, the lignocellulosic biomass that can be used in the present invention may be materials that do not compete with food.

The lignocellulosic biomass may further contain starch in addition to the above-described lignocellulose. The ratio between the starch and lignocellulose components in such biomass may vary depending on the type, and examples thereof include rice straw, rice husk, corn fiber (fiber of corn shells), corn stover (stems and leaves of corn), tapioca starch pulp (starch pulp generated when producing starch from cassava rhizomes), and the like. In the case of lignocellulosic biomass including starch, if hot water or other solvents are used in pretreatment, the starch flows into liquid during the treatment, which may lead to the loss of material. In contrast, if with finely pulverizing treatment, such a problem can be avoided, and the amount of ethanol produced can be increased with yeast displaying enzymes on the cell surface.

Surface Displaying Yeast

There is no particular limitation on the host yeast as long as ethanol fermentation can be performed using glucose as a substrate. The yeast is preferably yeast belonging to the genus *Saccharomyces*, and more preferably *Saccharomyces cerevisiae*. Examples of the strain of *Saccharomyces cerevisiae* include *Saccharomyces cerevisiae* NBRC1440 strain (available from the National Institute of Technology and Evaluation), *Saccharomyces cerevisiae* TJ14 strain (Moukamnerd et al., Appl. Microbiol. Biotechnol., 2010, Vol. 88, p. 87-94), and *Saccharomyces cerevisiae* KF-7 strain (Tang et al., Process Biochem., 2006, Vol. 41, p. 909-914).

As the enzyme that is displayed on the surface, enzymes involved in hydrolysis of the lignocellulosic biomass may be used. Examples of the enzymes include at least one type of enzyme selected from the group consisting of endoglucanase, cellobiohydrolase, β-glucosidase, ferulic acid esterase, β-galactosidase, pectinase, xylanase, xylosidase, acetylxylan esterase, arabinofuranosidase, swollenin, laccase, lignin peroxidase, glucoamylase, α-amylase, β-amylase, and pullulanase. When using a plurality of types of enzymes, there is no limitation on the types of enzymes that are to be combined. Also, there is no particular limitation on the integration copy number of enzyme genes.

The endoglucanase (endo β1,4-glucanase) is also referred to as "cellulase" in a narrow sense, and cleaves cellulose intramolecularly to produce glucoses, cellobioses, and cellooligosaccharides (having a degree of polymerization of 3 or more and preferably 10 or less, but there is no limitation to this). The endoglucanase has a higher reactivity to cellulose with low or no crystallinity, such as non-crystallized cellulose, soluble cellooligosaccharide, and cellulose derivatives (e.g., carboxymethyl cellulose (CMC)), but a lower reactivity to cellulose microfibrils having a crystalline structure. The endoglucanase is an example of the enzyme that hydrolyzes non-crystalline cellulose. There are a plurality of types of endoglucanase, and examples thereof include, but are not limited to, *Trichoderma reesei*-derived endoglucanase (in particular, EGI and EGII).

The cellobiohydrolase degrades cellulose from either its reducing end or non-reducing end to produce cellobioses. The cellobiohydrolase degrades crystalline cellulose such as cellulose microfibrils having a crystalline structure, but its reactivity to cellulose with a low crystallinity or no crystallinity, such as cellulose derivatives (e.g., carboxymethyl cellulose (CMC)) is low. The cellobiohydrolase is an example of the enzyme that hydrolyzes crystalline cellulose. Due to a rigid structure resulting from dense intermolecular and intramolecular hydrogen bonds of crystalline cellulose, the hydrolysis rate of crystalline cellulose by the cellobiohydrolase is slower than the hydrolysis rate of non-crystalline cellulose by the endoglucanase. There are two types of cellobiohydrolase, which are respectively referred to as cellobiohydrolase I (CBHI) and cellobiohydrolase II (CBHII). Examples of the cellobiohydrolase include, but are not limited to, *Trichoderma reesei*-derived cellobiohydrolase (in particular, CBHII) and *Phanerochaete chrysosporium*-derived cellobiohydrolase (in particular, CBHI).

The β-glucosidase is an exo-type hydrolyzing enzyme that separates a glucose unit from its non-reducing end in cellulose. The β-glucosidase cleaves a β-1,4-glucosidic bond between an aglycone or a sugar chain and β-D-glucose, and hydrolyzes cellobiose or cellooligosaccharide to produce glucose. The β-glucosidase is an example of an enzyme that hydrolyzes cellobiose or cellooligosaccharide. Nowadays, one type of β-glucosidase is known and is referred to as β-glucosidase 1. Examples of the β-glucosidase include, but are not limited to, *Aspergillus aculeatus*-derived β-glucosidase (in particular, BGL1).

The ferulic acid esterase is an enzyme that causes an esterification reaction between ferulic acid and glycerol. The ferulic acid esterase exhibits an action of hydrolyzing ferulic acid that links lignin to polysaccharide in lignocellulosic biomass. This action allows the structure of the lignocellulosic biomass to be loosened (that is, a portion of the structure of the lignocellulosic biomass to be degraded), so that it is possible to facilitate the saccharification by the cellulose-hydrolyzing enzyme preparation. Examples of the ferulic acid esterase include, but are not particularly limited to, ferulic acid esterases derived from the genus *Aspergillus* (e.g., *Aspergillus oryzae* and *Aspergillus niger*), the genus *Penicillium* (e.g., *Penicillium chrysogenum*), and the genus *Talaromyces* (e.g., *Talaromyces funiculosus*). Examples of a gene coding for ferulic acid esterase include a *Talaromyces funiculosus*-derived gene (FaeA: GenBank Accession Number: AJ312296) and an *Aspergillus oryzae*-derived gene (FaeA: GenBank Accession Number: AO090001000207).

For hydrolysis of the starch, the yeast may be any one that expresses a starch-hydrolyzing enzyme (e.g., α-amylase, glucoamylase, β-amylase, or pullulanase, etc.). The mode of expression may be surface display or may be secretory. The expressed enzyme may be a combination of enzymes having different modes of hydrolysis in the yeast. Preferably, the yeast displays at least one starch-hydrolyzing enzyme on the cell surface. In one embodiment, the surface displaying yeast used in the present invention is yeast secreting α-amylase and displaying glucoamylase on the cell surface.

Glucoamylase is officially referred to as glucan 1,4-α-glucosidase, and is also referred to as 1,4-α-D-glucan glucohydrolase, exo 1,4-α-glucosidase, γ-amylase, lysosomal α-glucosidase, or amyloglucosidase. Glucoamylase hydrolyzes an α-1,4-bond at the non-reducing end of a sugar chain in an exo manner, to produce one molecule of dextrose. There is also known glucoamylase that cleaves an α-1,6-bond. Examples of the glucoamylase include, but are not limited to, *Rhizopus oryzae*-derived glucoamylase (GenBank Accession Number: D00049.1).

Alpha-amylase is also referred to as 1,4-α-D-glucan glucanohydrolase or glycogenase, and is an enzyme that irregularly cleaves an α-1,4-bond of starch or glycogen to produce polysaccharide, maltose, or oligosaccharide. It is a general enzyme widely distributed in animals, plants, and microorganisms. Examples of the α-amylase include, but are not limited to, *Streptococcus bovis*-derived α-amylase (GenBank Accession Number: D000829.1).

In this manner, the surface displaying yeast used in the method of the present invention may be further subjected to genetic recombination so as to express a gene in a mode other than surface display.

The surface displaying yeast used in the method of the present invention may be yeast having xylose metabolizing ability. For example, if *Saccharomyces cerevisiae* is used as a host, this yeast can typically utilize glucose, which is a hexose, but cannot utilize xylose, which is a pentose. It is possible to use *Saccharomyces cerevisiae* modified through selection screening, mutation induction, genetic recombination, or the like so as to be capable of utilizing xylose. *Saccharomyces cerevisiae* may be transformed so as to have a xylose-utilizing gene. Examples of the xylose-utilizing gene include a gene of a xylose-metabolizing enzyme, such as a xylose reductase (XR) gene (e.g., derived from *Pichia stipitis*: INSD Accession No. X59465 or A16164), a xylitol dehydrogenase (XDH) gene (e.g., derived from *Pichia stipitis*: INSD Accession No. X55392 or A16166), and a xylulokinase (XK) gene (e.g., derived from *Saccharomyces cerevisiae*: INSD Accession No. X82408). *Saccharomyces cerevisiae* can be recombinantly engineered so as to express these three genes.

The gene coding for the above-described enzyme can be obtained, for example, through amplification by a polymerase chain reaction (PCR) using a pair of primers prepared based on the sequence information of the structural gene with a genome DNA or cDNA prepared from an organism from which the enzyme is derived as a template.

In the present invention, as the method for displaying an enzyme on the yeast cell surface, methods known to a person skilled in the art can be adopted, and, for example, a GPI anchor (Japanese Laid-Open Patent Publication No. H11-290078) or a sugar chain-binding domain (WO 02/085935) of a cell-surface localized protein can be used. Examples of the cell-surface localized protein used in these methods include α- or α-agglutinin (flocculation protein of yeast), FLO protein (e.g., FLO1, FLO2, FLO4, FLO5, FLO9, FLO10, and FLO11) and alkaline phosphatase. Yeast (*Saccharomyces cerevisiae*)-derived TIR1 (cell wall mannoprotein induced in cold shock or anaerobic state. Kitagaki et al., Eur. J. Biochem., 1997, Vol. 249(1), p. 343-349) can also be used.

Examples of the method for displaying an enzyme on the cell surface using the GPI anchor include a method using a recombinant DNA constituted of a DNA coding for a secretion signal sequence—a gene of interest—a DNA coding for a GPI anchor adhesion recognition signal. Glucoamylase which is expressed from this recombinant DNA and is secreted out of the cell membrane can be bound to the GPI anchor of the cell membrane via the GPI anchor adhesion recognition signal. As the GPI anchor adhesion recognition signal sequence, a GPI anchor adhesion recognition signal sequence that exists in the sequence of 320 amino acids from the C-terminus of yeast α-agglutinin can be used, for example.

Examples of the method for displaying an enzyme on the cell surface using the sugar chain-binding domain include a method using a recombinant DNA prepared so as to express a fusion protein by linking the enzyme on the side of the N-terminus or C-terminus, or both the sides of N- and C-termini of the cell-surface localized protein (flocculation functional domain). The enzyme which is expressed from this recombinant DNA and is secreted out of the cell membrane can anchor on the cell surface because a plurality of sugar chains in the sugar chain-binding domain interact with the sugar chains in the cell wall. Examples of the flocculation functional domain include a sugar chain-binding domain of lectin, lectin-like protein or the like, and typically the flocculation functional domain of the GPI anchor protein.

If yeast-derived TIR1 is used, a recombinant DNA can be prepared so as to express a fusion protein via a linkage between the N-terminus of the enzyme of interest and the C-terminus of the TIR1.

There is no particular limitation on the secretion signal sequence used in the recombinant DNA, and it may be a secretion signal of the enzyme, a secretion signal sequence of the cell-surface localized protein, or another secretion signal sequence capable of leading the enzyme out of the cell. A part or the whole of the secretion signal sequence and pro-sequence may remain in the N-terminus after the enzyme is displayed on the cell surface as long as there is no influence on the enzyme activity.

Preferably, the enzyme is displayed on the cell surface of the yeast such that a substrate-binding domain of the enzyme is oriented outward from the cell. In order to realize the outward orientation, the surface display techniques as described above can be selected depending on the position of the substrate-binding domain (e.g., whether it is positioned in the N-terminal side or in the C-terminal side of the enzyme protein). For the surface display of an enzyme having the substrate-binding domain in the N-terminal side, for example, it is possible to use a recombinant DNA prepared so as to express a fusion protein via a linkage between the C-terminus of the enzyme and the N-terminus of the anchor protein based on α-agglutinin. In the surface display of an enzyme having the substrate-binding domain on the C-terminus side, for example, it is possible to use a recombinant DNA prepared so as to express a fusion protein in which the N-terminus of the enzyme is bound to the C-terminus of the anchor protein based on yeast-derived TIR1.

The enzyme can be secreted from the yeast, for example, by introducing, into the yeast, a recombinant DNA in which the gene coding for the enzyme of interest is ligated downstream of the DNA coding for the above-described secretion signal sequence. The enzyme can be expressed in the cell of yeast, for example, by preparing a recombinant DNA without linking to the secretion signal sequence or without applying the surface display technique, and introducing the recombinant DNA into the yeast.

The synthesis and linkage of the above-described recombinant DNA can be performed, for example, by a method usually used by a person skilled in the art. A linker may be used as necessary for linkage of the DNA as appropriate.

The above-described recombinant DNA may be incorporated into an expression vector. Such an expression vector is, for example, in a plasmid form. For example, a plasmid having the replication origin (Ori) of the yeast 2 μm plasmid and the replication origin of ColE1 is preferably used. It is preferable that the plasmid has a selective marker and a replication gene for *Escherichia coli* in that the plasmid preparation and the detection of transformant are facilitated. Examples of the selective marker include a drug resistance gene and an auxotrophic gene. Examples of the drug resistance gene include, but are not particularly limited to, the ampicillin resistance gene (Ampr) and the kanamycin resistance gene (Kanr) Examples of the auxotrophic gene include, but are not particularly limited to, the N-(5'-phosphoribosyl)anthranilate isomerase (TRP1) gene, tryptophan synthase (TRP5) gene, β-isopropylmalate dehydrogenase (LEU2) gene, imidazoleglycerol-phosphate dehydrogenase (HIS3) gene, histidinol dehydrogenase (HIS4) gene, dihydroorotate dehydrogenase (URA1) gene, and orotidine-5-phosphate decarboxylase (URA3) gene. A replication gene for yeast may be selected as necessary.

It is preferable that the expression vector has a promoter and a terminator suitable for expressing the gene coding for an enzyme of interest for yeast. Examples of the promoter and the terminator include, but are not particularly limited to, the promoters and the terminators of GAPDH (glyceraldehyde 3'-phosphate dehydrogenase), PGK (phosphoglycerate kinase), PYK (pyruvate kinase) and TPI (triosephosphate isomerase). The gene coding for an enzyme of interest is inserted between the promoter and the terminator.

There is no particular limitation on the method for introducing the recombinant DNA into yeast. Examples thereof include a lithium acetate method, an electroporation method and a protoplast method. The introduced recombinant DNA may exist, for example, in a plasmid form, or in a form in which the recombinant DNA is inserted into the yeast chromosome or is incorporated into the yeast chromosome by a homologous recombination.

Yeast into which the recombinant DNA has been introduced is selected by using the selective marker, and measuring the activity of the expressed enzyme. For example, an antibody against an enzyme of interest can be used to confirm that the enzyme is displayed on the cell surface.

Production of Ethanol

In this specification, a step of culturing yeast in a medium containing a fermentation substrate, thereby producing ethanol is also referred to as "fermentation step" for convenience. The term "fermentation substrate" in this specification refers to a substrate in the fermentation step.

As the fermentation substrate, lignocellulosic biomass particles may be used. The lignocellulosic biomass particles have an average particle size of for example, 2 to 600 µm, preferably 10 to 200 µm, and more preferably 20 to 100 µm. Furthermore, the lignocellulosic biomass particles are preferably subjected to particle size regulation so as to have, in addition to the average particle size, a half width (d50) of the particle size distribution of preferably 200 µm or less, and more preferably 20 µm or more and 100 µm or less. The average particle size of the lignocellulosic biomass particles is such that 50% of all particles is 200 µm or less and 90% thereof is 600 µm or less, preferably such that 50% of all particles is 100 µm or less and 90% thereof is 200 µm or less, and more preferably such that 50% of all particles is 50 µm or less and 90% thereof is 100 µm or less. There is no particular limitation on the method and means for the particle size regulation, and they may be selected as appropriate by a person skilled in the art.

The lignocellulosic biomass particles may be prepared, for example, by performing finely pulverizing treatment on the lignocellulosic biomass.

The "finely pulverizing treatment" is a method for finely pulverizing the lignocellulosic biomass using a mill or the like. There are many types of mills for performing the finely pulverizing treatment. For example, a ball mill is often used. This is a device in which balls are placed in a container and a sample is pulverized through vibration and rotation, wherein, typically, the container can be hermetically closed, and the treatment can be performed not only under dry conditions but also in gas atmospheres or under wet conditions. The pulverization using the ball mill is of a batch type, but, as devices capable of performing continuous pulverization, there are devices having different pulverizing mechanisms, such as a cutter mill, a hammer mill, a roll mill, a disc mill, or the like. Considering the optimum size of sample introduced into a mill, it is effective to finely pulverize a sample in a stepwise manner using a plurality of devices according to the shape or the size of the sample.

For example, as a mill for high impact and energy conservation, a tandem-ring mill using the ring-type pulverizing medium tumbling method has been developed (Non-Patent Document 2). In this device, a ring, which is a pulverizing medium, tumbles along the inner wall of the container to exert a centrifugal force on the material for fine pulverization. For example, this device can be preferably used in the finely pulverizing treatment in the case where wood (e.g., cedarwood) is used as lignocellulosic biomass.

Examples of the other mills include a nano-mech REACTOR (Simoloyer®, manufactured by Zoz GmbH, available from Techno-Eye Inc.: balls are used as milling media and a rotor is rotated at high rate to cause high-impact collision, thereby exerting an energy to pulverize biomass), and a Wonder Blender (manufactured by Osaka Chemical Co., Ltd.).

The lignocellulosic biomass particles may be subjected as necessary to hydrothermal treatment before or after the finely pulverizing treatment of the lignocellulosic biomass.

The "hydrothermal treatment" is treatment with water at a high temperature as necessary under pressure (e.g., contact, immersion, or steaming). For example, the lignocellulosic biomass is cut or pulverized as necessary and is mixed with water to a content of for example, about 20% by weight (dry weight), and this mixture is thermally treated. The thermal treatment is performed at 120° C. to 300° C., preferably 150° C. to 280° C., and more preferably 180° C. to 250° C., for 15 seconds to 1 hour. The treatment temperature and time may vary depending on the biomass used, and an increase in the treatment temperature may shorten the treatment time. A pressure may be applied during the thermal treatment. The applied pressure may be set automatically by the device or manually to any pressure with which a temperature within the above-described range is realized.

The product obtained after the end of the hydrothermal treatment may be as appropriate cooled down and dried. There is no particular limitation on the drying method. Examples thereof include freeze drying, low-temperature drying, room-temperature drying, high-temperature drying, and the like, and drying may be carried out under ventilation or under reduced pressure.

The fermentation step may be performed by culturing yeast in a medium containing a fermentation substrate (preferably liquid culture). The fermentation step may be performed under ordinary conditions for ethanol fermentation.

The fermentation medium may further contain components necessary or desirable for growth of the yeast. The temperature during the reaction in the fermentation step may depend on the yeast used, but it may be, for example, 30° C. to 37° C., and preferably 30° C. to 35° C. The fermentation pH is, for example, 4 to 8, and preferably 5 to 7. The fermentation culture may be anaerobically performed (dissolved oxygen concentration may be, for example, 1 ppm or less, more preferably about 0.3 ppm or less, and even more preferably 0.1 ppm or less).

Examples of the form of the fermentation step include a batch process, a feed-batch process, a repetitive batch process, a continuous process, and the like, and any of such processes may be selected.

The amount of yeast input (the yeast cell concentration at the start of fermentation) and the amount of fermentation substrate initially fed as well as the amount and time of fermentation substrate additionally fed as necessary and the fermentation time period may be determined as appropriate according to the type and state of substrate, the volume of fermentation culture, the intended amount of fermentation ethanol to be produced, and other factors. The yeast cell concentration at the start of fermentation is, for example, 2 g to 20 g wet weight/L ($1 \times 10^7$ cells/mL to $1 \times 10^8$ cells/mL), and preferably 4 g to 10 g wet weight/L ($2 \times 10^7$ cells/mL to $0.5 \times 10^8$ cells/mL). The initially fed amount is, for example, 5 (w/v) % to 50 (w/v) %, and preferably 10 (w/v) % to 25 (w/v) %, with respect to the liquid fermentation (the total of the medium and the cells used for fermentation). The amount and time of fermentation substrate additionally fed may be determined while monitoring the viscosity of the fermentation medium, the amount of ethanol produced, the amount of carbon dioxide generated, and the like during the course of fermentation.

In the method for producing ethanol in the present invention, an enzyme that hydrolyzes cellulose or starch (e.g., cellulase enzyme, starch-degrading enzyme, or both) may be supplementarily used. The "cellulase enzyme" or "starch-degrading enzyme" includes any form that is isolated as an enzyme. Examples of the "cellulase enzyme" include an enzyme isolated and purified from a microorganism that produces cellulase (e.g., endoglucanase) as described above and an enzyme produced by genetic recombination using a cellulase gene. Examples of the "starch-degrading enzyme" include an enzyme isolated and purified from a microorganism that produces a starch-degrading enzyme (e.g., α-amylase, glucoamylase, β-amylase, pullulanase, etc.) as described above and an enzyme produced by genetic recombination using a gene coding for an enzyme. Commercially available enzymes can be used. Examples of the commercially available cellulase enzymes include Cellic CTec2 (manufactured by Novozymes), Accellerase (manufactured by Genencor), and Meicelase (manufactured by Meiji Seika Pharma Co., Ltd.). Commercially available enzymes can be used. Examples of the commercially available amylase enzymes include Cellic CTec2 (manufactured by Novozymes), Accellerase (manufactured by Genencor), and Meicelase (manufactured by Meiji Seika Pharma Co., Ltd.). Examples of the commercially available starch-degrading enzymes include Neo-Spitase (liquefied α-amylase (manufactured by Nagase ChemteX Corporation)), Glucozyme (glucoamylase (manufactured by Nagase ChemteX Corporation)), Promozyme (pullulanase (manufactured by Novozymes), and the like. For example, prior to the fermentation step, the fermentation substrate may be previously incubated with the cellulase enzyme (or the starch-degrading enzyme, or both enzymes, as necessary) under appropriate conditions. The amount of cellulase enzyme added may be, for example, 1 to 20% by weight, and preferably 3 to 10% by weight, with respect to the weight of the fermentation substrate. The amount of starch-degrading enzyme added may be, for example, 0.01 to 2% by weight, and preferably 0.1 to 1% by weight, with respect to the weight of the fermentation substrate.

Since the fermentation conditions of ethanol vary during the course of fermentation, it is preferable to control the conditions within a certain range. The time course of fermentation may be monitored, for example, by any means commonly used by a person skilled in the art, such as gas chromatography, HPLC, or the like.

The yeast and, as necessary, the cellulase enzyme for the reaction with the fermentation substrate are preferably immobilized on a support. Accordingly, they can be used again.

As the support and the method for immobilization, a support and a method commonly used by a person skilled in the art are used. Examples of the immobilizing method include support binding, entrapment, crosslinking, and the like.

As the support, a porous material is preferably used. Preferable examples thereof include foams and resins such as polyvinyl alcohol, polyurethane foam, polystyrene foam, polyacrylamide, porous polyvinyl formal resin, silicone foam, and the like. The pore size of the porous material may be determined in consideration of the used microorganism and the size thereof. In the case of practical yeast, the size is preferably 50 to 1000 μm.

The support may have any shape. Considering the strength of the support, culturing efficiency, and the like, the support is preferably in the shape of a sphere or a column (e.g., a cube). The size may be determined according to the used microorganism. It is generally preferable that the diameter is 2 to 50 mm if the carrier is in the shape of a sphere, and one side has a length of 2 to 50 mm if the carrier is in the shape of a column.

After the fermentation step, the medium which contains ethanol is removed from the fermenter and ethanol is isolated from the medium by the separation process commonly used by a person skilled in the art, such as a separation operation using a centrifuge or a distillation operation.

EXAMPLES

Hereinafter, the present invention will be described by way of examples, but the present invention is not limited to the examples.

Procedures performed in the examples shown below will be described in reference examples. Reference Examples 1 to 3, 6, and 7 show a procedure of pretreatment for finely pulverizing lignocellulosic biomass. Reference Example 4 shows a procedure of hydrothermal treatment performed on rice straw and bagasse. Reference Example 5 shows a procedure of saccharification and fermentation.

For the fermentation, yeast *Saccharomyces cerevisiae* NBRC1440 strain (obtained from the National Institute of Technology and Evaluation) and TJ14 strain (Moukamnerd et al., Appl. Microbiol. Biotechnol., 2010, Vol. 88, p. 87-94), and recombinant yeasts shown in Preparation Examples 1 to 12 are used.

All PCR amplification shown in these examples was performed by using PrimeSTAR MAX DNA Polymerase (Takara Bio Inc.). All yeast transformation shown in these examples was performed by using a lithium acetate method. As reagents shown in these examples, reagents usually used by a person skilled in the art were used unless otherwise described.

Reference Example 1: Lignocellulosic Biomass Finely Pulverizing Treatment 1

Lignocellulosic biomass cut to have a length of 1 mm was pulverized for 100 minutes using a φ252 hole gear-type pulverizing medium tumbling mill (Non-Patent Document 2), at a mill container diameter of φ284, a number of vibrations of 1600 cpm, an amplitude of 7 mm, and a pulverization amount of 800 g.

Reference Example 2: Lignocellulosic Biomass Finely Pulverizing Treatment 2

Lignocellulosic biomass hydrothermally treated as in Reference Example 4 below was pulverized for 1 minute using a Wonder Blender (model: WB-1, manufactured by Osaka Chemical Co., Ltd.).

Reference Example 3: Lignocellulosic Biomass Finely Pulverizing Treatment 3

Cedarwood cut to have a length of 1 mm was finely pulverized for 30 minutes, 45 minutes, or 60 minutes, using a nano-mech REACTOR (model: CM01, Simoloyer®, manufactured by Zoz GmbH, obtained from Techno-Eye Inc.).

Reference Example 4: Lignocellulosic Biomass Hydrothermal Treatment

Lignocellulosic biomass was mixed with water to a content of about 20 (w/v) % (dry weight), and the mixture was placed in a hydrothermal treatment device (manufactured by Mitsubishi Heavy Industries, Ltd.) and treated at about 180° C. and about 3 MPa for 5 minutes to 20 minutes. Then, the solid content was isolated, and the isolated solid content was used as the fermentation substrate.

Reference Example 5: Saccharification and Fermentation

About 48 mL of enzymatic treatment solution (cellulase preparation Cellic CTec2 (manufactured by Novozymes) in an amount of 5 to 10% by weight with respect to the biomass dry weight, 2.5 mL of 1M citric acid buffer at pH 6, 10×YP (100 g/L yeast extract, 200 g/L polypeptone)) containing the pretreated lignocellulosic biomass (5 g in the dry weight in the case of a starting material concentration of 10%, 10 g in the dry weight in the case of a starting material concentration of 20%, and 15 g in the dry weight in the case of a starting material concentration of 30%) as the solid content was prepared.

This enzymatic treatment solution was put into a 50 mL plastic test tube (manufactured by Corning Incorporated) and then incubated at 50° C. at a rotation rate of 35 rpm using a thermoblock rotator (SN-06BN, manufactured by Nissinrika).

Seed culture of the above-described yeast was performed in a test tube containing 5 mL of YPD liquid culture medium (10 g/L yeast extract, 20 g/L polypeptone, and 20 g/L glucose) overnight, and the culture solution was then transferred into a flask containing 500 mL of YPD liquid culture medium, and a main culture was performed for 2 days. This culture solution was centrifuged (3000 rpm, 4° C., 10 minutes), and the yeast cells were washed twice with sterile distilled water, after which the yeast cells were suspended in sterile distilled water to a cell concentration of 100 g wet weight/L.

After 2 hours from the start of the enzymatic treatment, 48 mL of the enzymatic treatment solution was transferred into a 80 mL screw-cap bottle (manufactured by Duran). Furthermore, 2 mL of the yeast suspension was added thereto to a cell concentration of 20 g wet weight/L. After the addition of the yeast, the fermentation was started at 35° C.

The concentration of ethanol produced in the fermentation liquid (the enzymatic treatment solution to which the yeast suspension was added) was quantitated over time with an HPLC (High performance liquid chromatography system; Hitachi High-Tech Fielding Corporation, LaChrom Elite), using ULTRON PS-80H (manufactured by Shinwa Chemical Industries Ltd., 300 mm (L)×8 mm (ID)) as a separation column for the HPLC, ultrapure water (water purified with Milli-Q manufactured by Millipore Japan Corporation) as a mobile phase, and a refractive index detector as a detector, under the conditions of HPLC of a flow rate of 0.9 mL/minute and a column temperature of 50° C.

Preparation Example 1: Preparation of Yeast Displaying Cellulase on Cell Surface: Introduction of 2 Copies of Endoglucanase II (EGII), 1 Copy of Cellobiohydrolase II (CBHII or CBH2), and 1 Copy of β-Glucosidase (BGL) into NBRC1440 Strain As a first step, a plasmid pGK406EG (WO 2010/032762) was cleaved with StuI to have a linear form and introduced into NBRC1440/UHWL (WO 2010/032762), and a strain having no uracil auxotrophy was selected.

Next, as a second step, a plasmid pGK403EG (WO 2010/032762) was cleaved with NdeI to have a linear form and introduced into the strain selected in the first step, and a strain having no histidine auxotrophy was selected.

Furthermore, as a third step, a plasmid pILGP3-CBH2 (WO 2010/032762) was cleaved with HpaI to have a linear form and introduced into the strain selected in the second step, and a strain having no leucine auxotrophy was selected.

Lastly, as a fourth step, a plasmid pIWBGL (WO 2010/032762) was cleaved with Bst1107I to have a linear form and introduced into the strain selected in the third step, and a strain having no tryptophan auxotrophy was selected, which was taken as yeast of Preparation Example 1 displaying cellulase on the cell surface.

Note that the strain selected in the first step was named [NBRC1440/pGK406 EG], the strain selected in the second step was named [NBRC1440/pGK406 EG/pGK403 EG], the strain selected in the third step was named [NBRC1440/pGK406 EG/pGK403 EG/pILGP3-CBH2], and the strain selected in the fourth step was named [NBRC1440/pGK406 EG/pGK403 EG/pILGP3-CBH2/pIWBGL].

Preparation Example 2: Preparation of Yeast Displaying Endoglucanase on Cell Surface: Yeast Obtained by Engineering NBRC1440 Strain to Express Endoglucanase II (EGII) on Cell Surface The yeast (NBRC1440/pGK406 EG/pGK403 EG) obtained in the second step of Preparation Example 1 above was taken as yeast of Preparation Example 2 displaying cellulase on the cell surface.

Preparation Example 3: Preparation of Yeast Displaying β-Glucosidase on Cell Surface: Yeast Obtained by Engineering NBRC1440 Strain to Express β-Glucosidase (BGL) on Cell Surface As a first step, a fragment obtained by cleaving a plasmid pIWBGL with NotI, containing a GAPDH (glyceraldehyde triphosphate dehydrogenase) promoter, a secretion signal sequence of a *Rhizopus ozyzae*-derived glucoamylase gene, an *Aspergillus aculeatus*-derived BGL1 gene, the 3' half region of an α-agglutinin gene, and a GAPDH terminator was inserted to a NotI site of pRS406 (manufactured by Stratagene), so that a plasmid pRS406-BGL was formed.

Next, as a second step, PCR was performed using a primer SS-XbaI-Fw (Sequence ID No. 1) and a primer AG-XbaI-Rv (Sequence ID No. 2) with pIBG13 (WO 2010/032762) as a template to amplify the secretion signal sequence of the *Rhizopus ozyzae*-derived glucoamylase gene, the *Aspergillus aculeatus*-derived BGL1 gene, and the 3' half region of an α-agglutinin gene, and the resultant DNA chain was inserted to an XbaI site of pILGP3 (WO2010/032762A1) so that a plasmid pILGP3-BGL13 was formed.

Furthermore, as a third step, a plasmid pIWBGL was cleaved with Bst1107I to have a linear form and introduced into NBRC1440/UHWL, and a strain having no tryptophan auxotrophy was selected.

Furthermore, as a fourth step, the plasmid pRS406-BGL obtained in the first step was cleaved with NdeI to have a linear form and introduced into the strain selected in the third step, and a strain having no uracil auxotrophy was selected.

Furthermore, as a fifth step, the plasmid pILGP3-BGL13 obtained in the second step was cleaved with HpaI to have a linear form and introduced into the strain selected in the fourth step, and a strain having no leucine auxotrophy was selected, which was taken as yeast of Preparation Example 3 displaying β-glucosidase on the cell surface. As yeast of Preparation Example 3 displaying β-glucosidase on the cell surface, NBRC1440 having three copies of BGL was obtained.

The strain obtained in the third step was named [NBRC1440/pIWBGL], the strain obtained in the fourth step was named [NBRC1440/pIWBGL/pRS406-BGL], and the strain obtained in the fifth step was named [NBRC1440/pIWBGL/pRS406-BGL/pILGP3-BGL13].

The respective base sequences of the primers are as follows.

```
SS-XbaI-Fw:
                              (Sequence ID No. 1)
gctctagaATGCAACTGTTCAATTTGCC AG-XbaI-Rv:
                              (Sequence ID No. 2)
gctctagaTTTGATTATGTTCTTTCTATTTGAATGAG
```

Preparation Example 4: Preparation of Yeast Displaying Ferulic Acid Esterase on Cell Surface: Yeast Obtained by Engineering TJ14 Strain to Express Ferulic Acid Esterase (FaeA) on Cell Surface pGK406AG (Japanese Laid-Open Patent Publication No. 2011-142879) was used as a plasmid containing a promoter and a terminator necessary for gene expression and an α-agglutinin gene necessary for display on the yeast cell surface. In order to clone FaeA, the genomic DNA was extracted from cultured cells of *Talaromyces funiculosus*. PCR was performed using a primer SalI-ssFaeA-Fw (Sequence ID No. 3) containing a secretion signal sequence of a *Rhizopus oryzae*-derived glucoamylase gene and a primer SalI-FaeA-Rv (Sequence ID No. 4) with this genomic DNA as a template. The resultant gene fragment was digested with SalI and inserted to a SalI site of pGK406AG, so that a plasmid pGK406-ssFaeA-AG was formed.

The respective base sequences of the primers are as follows.

```
SalI-ssFaeA-Fw:
                              (Sequence ID No. 3)
ACGCGTCGACATGCAACTGTTCAATTTGCCATTGAAAGTTTCATTCTT

TCTCGTCCTCTCTTACTTTTCTTTGCTCGTTTCTCAGCAATCGCTATG

GGGCCAATGCGGTGGTAC

SalI-FaeA-Rv:
                              (Sequence ID No. 4)
ACGCGTCGACGTGGAATAGAGAGAAGAAACTCCAGATC
``` pAUR101 (manufactured by Takara Bio Inc.) was used as a vector for introduction into yeast. In order to insert a cassette containing a pGK promoter, a secretion signal sequence, FaeA, and α-agglutinin of the pGK406-ssFaeA-AG formed as described above into an SphI site of pAUR101, PCR was performed using a primer pAuR101-SphI-Fw (Sequence ID No. 5) and a primer pAuR101-SphI-Rv (Sequence ID No. 6) with pGK406-ssFaeA-AG as a template. This gene fragment was inserted into the pAUR101 cleaved with SphI, using an In-Fusion HD Cloning Kit (manufactured by Takara Bio Inc.), so that a plasmid pAUR101-pGK-ssFaeA-AG for display of FaeA on the yeast surface was formed. The pAUR101-pGK-ssFaeA-AG was cleaved with StuI and then used to transform yeast (*Saccharomyces cerevisiae* TJ14 strain) using a YEAST MAKER Yeast Transformation System (Clontech Laboratories, Palo Alto, Calif., USA), and an aureobasidin A-resistant strain was obtained. The resultant strain was taken as yeast of Preparation Example 4 displaying FaeA on the cell surface.

The respective base sequences of the primers are as follows.

```
pAuR101-SphI-Fw:
                              (Sequence ID No. 5)
CTCTGTTGAAGCTTGGTAATACGACTCACTATAGGG pAuR101-SphI-Rv:
                              (Sequence ID No. 6)
GAGTCGACCTGCAGGAATTAACCCTCACTAAAGGG
```

Preparation Example 5: Preparation of Xylose-utilizing Yeast: Yeast Obtained by Engineering TJ14 Strain to Express Three Types of Enzymes of Xylose Reductase (XR), Xylitol Dehydrogenase (XDH), and Xylulokinase (XK), "Yeast Expressing X3"

A plasmid pIUX1X2XK (Appl Microbiol Biotechnol. 2006 October; 72(6): 1136-43) was cleaved with PstI and introduced into a TJ14 strain having uracil auxotrophy imparted, and a strain having no uracil auxotrophy was selected, which was taken as xylose-utilizing yeast of Preparation Example 5. The resultant strain was named TJ14-pIUX3.

Preparation Example 6: Preparation of Yeast Utilizing Xylose and Displaying Ferulic Acid Esterase on Cell Surface: Yeast Obtained by Modifying TJ14 Strain to Express Three Types of Enzymes of Xylose Reductase (XR), Xylitol Dehydrogenase (XDH), and Xylulokinase (XK), and Express Ferulic Acid Esterase (FaeA) on the Cell Surface, "Yeast Expressing X3+Displaying FaeA on Cell Surface"

The plasmid pAUR101-pGK-ssFaeA-AG formed in Preparation Example 4 was cleaved with StuI and then used to transform the yeast TJ14-pIUX3 formed in Preparation Example 5, and an aureobasidin A-resistant strain was obtained. The resultant strain was taken as yeast of Preparation Example 6 utilizing xylose and displaying ferulic acid esterase on the cell surface.

Preparation Example 7: Preparation of Yeast Displaying N-Terminal Side of Cellobiohydrolase I (CBHI) on Cell Surface: Obtained by Engineering TJ14 Strain to Perform Surface Display Using Yeast-Derived α-Agglutinin, "CBHI-AG"

As a first step, *Phanerochaete chrysospoilum*-derived CBHI (hereinafter, PHCCBHI) was artificially synthesized based on the gene sequence of GenBank Accession Number: AAB46373 such that the moiety excluding the signal sequence of PHCCBHI was optimized for the codon used for *Saccharomyces cerevisiae*.

Next, as a second step, the PHCCBHI gene fragment obtained in the first step was amplified using a primer IF-SS-PHCCBHI-Fw (Sequence ID No. 7) and a primer IF-AG-PHCCBHI-Rv (Sequence ID No. 8).

Furthermore, as a third step, PCR was performed using a primer IF-101SphI-GAP-Fw (Sequence ID No. 9) and a primer IF-101SacI-AG-Rv (Sequence ID No. 10) with a plasmid pILGP3-CBH2 (WO2010/032762A1) as a template to amplify a GAPDH promoter, a secretion signal sequence of a *Rhizopus oryzae*-derived glucoamylase gene, a *Trichoderma reesei*-derived cellobiohydrolase (CBH2) gene, and the 3' half region of an α-agglutinin gene.

Furthermore, as a fourth step, the gene fragment obtained in the third step was inserted into PAUR101 (manufactured by Takara Bio Inc.) cleaved with SphI and SacI, using an In-Fusion HD Cloning Kit (manufactured by Takara Bio Inc.), so that a plasmid pAUR101-GP3-CBH2 was formed.

Furthermore, as a fifth step, PCR was performed using a primer AG-Fw (Sequence ID No. 11) and a primer SS-Rv (Sequence ID No. 12) with the plasmid pAUR101-GP3-CBH2 obtained in the fourth step as a template to amplify the moiety other than CBH2 so that CBH2 was removed.

Furthermore, as a sixth step, the PHCCBHI gene fragment obtained in the second step was inserted into the linear gene fragment obtained in the fifth step, using an In-Fusion HD Cloning Kit (manufactured by Takara Bio Inc.), so that a plasmid pAUR101-GP3-ssPHCCBHI-AG was formed.

The plasmid pAUR101-GP3-ssPHCCBHI-AG obtained in the sixth step was cleaved with StuI and then used to transform yeast TJ14 strain, and an aureobasidin A-resistant strain was obtained. The resultant strain was taken as yeast of Preparation Example 7 displaying the N-terminal side of cellobiohydrolase I (CBHI) on the cell surface.

The respective base sequences of the primers are as follows.

```
IF-SS-PHCCBHI-Fw:
                            (Sequence ID No. 7)
TCTTTGCTCGTTTCTGCTAATCACAGAACACTGACCAGTC IF-AG-PHCCBHI-Rv:
                            (Sequence ID No. 8)
AGAGCTTTTGGCGCTGTAGCATTGAGAGTAGTATGG IF-101SphI-GAP-Fw:
                            (Sequence ID No. 9)
CTCTGTTGAAGCTTGACCAGTTCTCACACGGAACAC IF-101SacI-AG-Rv:
                            (Sequence ID No. 10)
CGGCCAGTGAATTCGTTTGATTATGTTCTTTCTATTTGAATG AG-Fw:
                            (Sequence ID No. 11)
AGCGCCAAAAGCTCTTTTATC SS-Rv:
                            (Sequence ID No. 12)
CTTACTTTTCTTTGCTCGTTTCT
```

Preparation Example 8: Preparation of Yeast Displaying C-Terminal Side of Cellobiohydrolase I (CBHI) on Cell Surface: Obtained by Engineering TJ14 Strain to Perform Surface Display Using Yeast-Derived TIR1, "TIR-CBHI"

As a first step, PCR amplification was performed using a primer IF-SS-TIR1-Fw (Sequence ID No. 13) and a primer IF-TIR1-PHCCBHI-Rv (Sequence ID No. 14) with the genomic DNA of yeast TJ14 strain as a template, so that a TIR1 gene fragment containing no signal sequence was obtained.

Next, as a second step, PCR was performed using a primer TAA-dAG-Fw (Sequence ID No. 15) and a primer PHC-CBHI-dAG-Rv (Sequence ID No. 16) with the plasmid pAUR101-GP3-ssPHCCBHI-AG obtained in the sixth step of Preparation Example 7 as a template, so that the moiety other than α-agglutinin was amplified. Then, the resultant gene fragment was phosphorized with T4 Polynucleotide Kinase (Toyobo Co., Ltd.) and was then subjected to self-ligation, so that a plasmid pAUR101-GP3-ssPHCCBHI from which α-agglutinin was removed was formed.

Furthermore, as a third step, in order to insert the TIR1 gene fragment obtained in the first step between a secretion signal sequence of a *Rhizopus oryzae*-derived glucoamylase gene and PHCCBHI of the plasmid pAUR101-GP3-ssPH-CCBHI formed in the second step, PCR was performed using a primer PHCCBHI-Fw (Sequence ID No. 17) and a primer SS-Rv (Sequence ID No. 12), so that the gene fragment was made into a linear form.

Furthermore, as a fourth step, the TIR1 gene fragment obtained in the first step and the gene fragment obtained in the third step were ligated using an In-Fusion HD Cloning Kit, so that a plasmid pAUR101-GP3-ssTIR1-PHCCBHI was formed. This plasmid was made into a linear form by performing PCR using a primer 101-StuI-Fw (Sequence ID No. 18) and a primer 101-StuI-Rv (Sequence ID No. 19).

Lastly, the gene fragment obtained in the fourth step was used to transform yeast TJ14 strain, and an aureobasidin A-resistant strain was obtained. The resultant strain was taken as yeast of Preparation Example 8 displaying the C-terminal side of cellobiohydrolase I (CBHI) on the cell surface.

The respective base sequences of the primers are as follows.

```
IF-SS-TIR1-Fw:
                            (Sequence ID No. 13)
TTGCTCGTTTCTGCTCAAACCCAAGATCAAATTAACG IF-TIR1-PHCCBHI-Rv:
                            (Sequence ID No. 14)
CAGTGTTCTGTGATTTAACAACATAGCGGCAGCTGC TAA-dAG-Fw:
                            (Sequence ID No. 15)
TAAAACGGGTACTGTACAGTTAGTAC PHCCBHI-dAG-Rv:
                            (Sequence ID No. 16)
GTAGCATTGAGAGTAGTATGG PHCCBHI-Fw:
                            (Sequence ID No. 17)
AATCACAGAACACTGACCAGTC 101-StuI-Fw:
                            (Sequence ID No. 18)
CCTCCTATTACTGTCAAAGTGTTACCAG 101-StuI-Rv:
                            (Sequence ID No. 19)
CCTGCGGTCATCTGGAAAGTAC
```

Preparation Example 9: Preparation of Yeast Displaying N-terminal Side of Endoglucanase I (EGI) on Cell Surface: Display on Cell Surface of TJ14 Strain Using Yeast-Derived α-Agglutinin As a first step, *Trichoderma reesei*-derived EGI was artificially synthesized based on the gene sequence of GenBank Accession Number: P07981 such that the moiety excluding the signal sequence of EGI was optimized for the codon used for *Saccharomyces cerevisiae*.

Next, as a second step, the EGI gene fragment obtained in the first step was amplified using a primer IF-SS-EGI-Fw (Sequence ID No. 20) and a primer IF-EGI-AG-Rv (Sequence ID No. 21).

Furthermore, as a third step, the EGI gene fragment obtained in the second step and the linear gene fragment obtained in the fifth step of Preparation Example 7 (the linear gene fragment obtained by removing CBH2 from the plasmid pAUR101-GP3-CBH2) were ligated using an In-Fusion HD Cloning Kit (manufactured by Takara Bio Inc.), so that a plasmid pAUR101-GP3-ssEGI-AG was formed.

Lastly, the plasmid pAUR101-GP3-ssEGI-AG obtained in the third step was cleaved with StuI and then used to transform yeast TJ14 strain, and an aureobasidin A-resistant strain was obtained. The resultant strain was taken as yeast of Preparation Example 9 displaying the N-terminal side of endoglucanase I (EGI) on the cell surface.

The respective base sequences of the primers are as follows.

```
IF-SS-EGI-Fw:
                                        (Sequence ID No. 20)
TCTTTGCTCGTTTCTGCTCAACAACCTGGTACCTCTAC IF-EGI-AG-Rv:
                                        (Sequence ID No. 21)
AGAGCTTTTGGCGCTTAAGCATTGAGAGTAGTAATCATTG
```

Preparation Example 10: Preparation of Yeast Displaying C-Terminal Side of Endoglucanase I (EGI) on Cell Surface: Display on Cell Surface of TJ14 Strain Using Yeast-Derived TIR1

As a first step, PCR amplification was performed using a primer IF-SS-TIR1-Fw (Sequence ID No. 13) and a primer IF-TIR1-EGI-Rv (Sequence ID No. 22) with the genomic DNA of TJ14 as a template, so that a TIR1 gene fragment containing no signal sequence was obtained.

Next, as a second step, PCR was performed with a template constituted by the plasmid pAUR101-GP3-ssEGI-AG obtained in the third step of Preparation Example 9, using a primer TAA-dAG-Fw (Sequence ID No. 15) and a primer EGI-dAG-Rv (Sequence ID No. 23), so that the moiety other than α-agglutinin was amplified. Then, the resultant gene fragment was phosphorized with T4 Polynucleotide Kinase (Toyobo Co., Ltd.) and was then subjected to self-ligation, so that a plasmid pAUR101-GP3-ssEGI from which α-agglutinin was removed was formed.

Furthermore, as a third step, in order to insert TIR1 between a secretion signal sequence of a Rhizopus oryzae-derived glucoamylase gene and PHCCBHI of the plasmid pAUR101-GP3-ssEGI obtained in the second step, PCR was performed using a primer EGI-Fw (Sequence ID No. 24) and a primer SS-Rv (Sequence ID No. 12), so that the gene fragment was made into a linear form.

Furthermore, as a fourth step, the TIR1 gene fragment obtained in the first step and the gene fragment obtained in the third step were ligated using an In-Fusion HD Cloning Kit, so that a plasmid pAUR101-GP3-ssTIR1-EGI was formed.

Furthermore, as a fifth step, PCR was performed using a primer 101-StuI-Fw (Sequence ID No. 18) and a primer 101-StuI-Rv (Sequence ID No. 19) with the plasmid pAUR101-GP3-ssTIR1-EGI obtained in the fourth step as a template, so that the gene fragment was made into a linear form.

Lastly, the gene fragment obtained in the fifth step was used to transform yeast TJ14 strain, and an aureobasidin A-resistant strain was obtained. The resultant strain was taken as yeast of Preparation Example 10 displaying the C-terminal side of endoglucanase I (EGI) on the cell surface.

The respective base sequences of the primers are as follows.

```
IF-TIR1-EGI-Rv:
                                        (Sequence ID No. 22)
GGTACCAGGTTGTTGTAACAACATAGCGGCAGCTGC EGI-dAG-Rv:
                                        (Sequence ID No. 23)
TAAGCATTGAGAGTAGTAATCATTG EGI-Fw:
                                        (Sequence ID No. 24)
CAACAACCTGGTACCTCTAC
```

Preparation Example 11: Preparation of Yeast Displaying C-Terminal Side of Ferulic Acid Esterase on Surface: Display on Cell Surface of TJ14 Strain Using Yeast-Derived TIR1

As a first step, PCR amplification was performed using a primer IF-SS-TIR1-Fw (Sequence ID No. 13) and a primer IF-TIR1-FaeA-Rv (Sequence ID No. 25) with the genomic DNA of yeast TJ14 strain as a template, so that a TIR1 gene fragment containing no signal sequence was obtained.

Next, as a second step, PCR was performed using a primer TAA-dAG-Fw (Sequence ID No. 15) and a primer FaeA-dAG-Rv (Sequence ID No. 26) with the plasmid pAUR101-pGK-ssFaeA-AG for display of FaeA on the yeast surface used in Preparation Example 4 as a template, so that the moiety other than α-agglutinin of the plasmid pAUR101-pGK-ssFaeA-AG for display of FaeA on the yeast cell surface was amplified. Then, the resultant gene fragment was phosphorized with T4 Polynucleotide Kinase (Toyobo Co., Ltd.) and was then subjected to self-ligation, so that a plasmid pAUR101-pGK-ssFaeA from which α-agglutinin was removed was formed.

Furthermore, as a third step, in order to insert TIR1 between a secretion signal sequence of a Rhizopus oryzae-derived glucoamylase gene and FaeA of the plasmid pAUR101-pGK-ssFaeA obtained in the second step, PCR was performed using a primer FaeA-Fw (Sequence ID No. 27) and a primer SS-Rv (Sequence ID No. 12) with the plasmid pAUR101-pGK-ssFaeA as a template, so that the gene fragment was made into a linear form.

Furthermore, as a fourth step, the TIR1 gene fragment obtained in the first step and the gene fragment obtained in the third step were ligated using an In-Fusion HD Cloning Kit, so that a plasmid pAUR101-pGK-ssTIR1-FaeA was formed. This plasmid was made into a linear form by performing PCR using a primer 101-StuI-Fw (Sequence ID No. 18) and a primer 101-StuI-Rv (Sequence ID No. 19).

Lastly, the gene fragment obtained in the fourth step was used to transform yeast TJ14 strain, and an aureobasidin A-resistant strain was obtained. The resultant strain was taken as yeast of Preparation Example 11 displaying the C-terminus side of ferulic acid esterase on the cell surface.

The respective base sequences of the primers are as follows.

```
IF-TIR1-FaeA-Rv:
                                        (Sequence ID No. 25)
CCATAGCGATTGCTGTAACAACATAGCGGCAGCTGC
```

-continued

FaeA-dAG-Rv:
(Sequence ID No. 26)
GTGGAATAGAGAGAAGAAACTC

FaeA-Fw:
(Sequence ID No. 27)
CAGCAATCGCTATGGGGCCAATG

Example 1: Comparison Between Ethanol Fermentations of Hydrothermally Treated Rice Straw and Finely Pulverized Rice Straw For rice straw, finely pulverizing treatment and hydrothermal treatment were performed according to Reference Examples 1 and 4, respectively, to obtain fermentation substrates. These respective treated materials were taken as fermentation substrates, and saccharified and fermented according to Reference Example 5, using each of wild-type yeast (NBRC1440 strain) and the recombinant yeast of Preparation Example 1 (NBRC1440 strain into which 2 copies of endoglucanase, 1 copy of cellobiohydrolase, and 1 copy of β-glucosidase were introduced). The material concentration of the pretreated rice straw was set to 10 (w/v) % with respect to the liquid fermentation, and a commercially available cellulase preparation (C-Tec2) was used in an amount of 5% by weight with respect to the weight of the pretreated material. The yeast cell concentration was set to 20 g wet weight/L with respect to the liquid fermentation.

FIG. 1 shows graphs of ethanol fermentation results of hydrothermally treated rice straw (a) and finely pulverized rice straw (b) respectively, using each of wild-type yeast (NBRC1440 strain) and the recombinant yeast of Preparation Example 1. The vertical axis indicates the ethanol concentration (g/L) in a liquid fermentation, and the horizontal axis indicates the fermentation time (hours). The symbols in the graphs are as follows: a white circle represents wild-type yeast; and a black circle represents recombinant yeast of Preparation Example 1.

As shown in FIG. 1(a), when hydrothermally treated rice straw was taken as a fermentation substrate, the ethanol yield was not increased even using yeast displaying cellulase on the cell surface (an increase in the ethanol concentration was not seen due to saccharification facilitation by cellulase displayed on the cell surface) at an initial cell concentration (20 g wet weight/L) lower than 100 g wet weight/L described in Non-Patent Document 4. On the other hand, as shown in FIG. 1(b), when finely pulverized rice straw was taken as a fermentation substrate, the ethanol concentration was increased compared with that of the wild-type yeast, even at a low initial cell concentration such as 20 g wet weight/L, because cellulase on the cell surface enhanced saccharification.

Example 2: Ethanol Fermentation of Finely Pulverized Rice Straw by Yeast Expressing Single Enzyme on Cell Surface Rice straw was finely pulverized according to Reference Example 1 to obtain a fermentation substrate. The resultant fermentation substrate was saccharified and fermented according to Reference Example 5, using each of wild-type yeast (NBRC1440 strain and TJ14 strain) and the recombinant yeasts shown in Preparation Examples 2 to 4 (i.e., the yeast obtained by engineering NBRC1440 strain to express endoglucanase II (EGII) on the cell surface; the yeast obtained by engineering NBRC1440 strain to express β-glucosidase (BGL) on the cell surface; and the yeast obtained by engineering TJ14 strain to express ferulic acid esterase (FaeA) on the cell surface). The resultant fermentation substrate was fed in a concentration of 20 (w/v) % with respect to the liquid fermentation, and a commercially available cellulase preparation (C-Tec2) was used in an amount of 5% by weight with respect to the weight of the finely pulverized material. The yeast cell concentration was set to 20 g wet weight/L with respect to the liquid fermentation.

Figure 2:
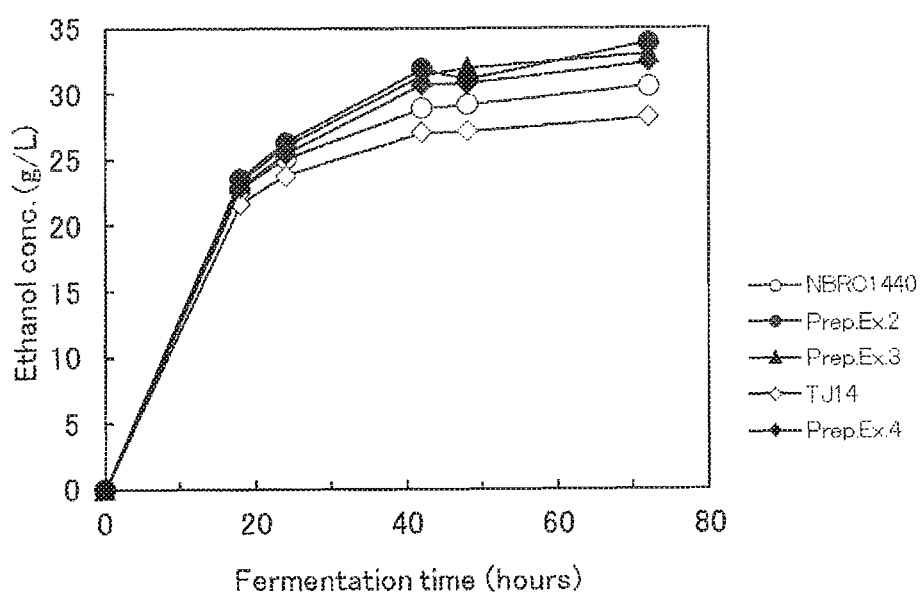
FIG. 2 shows a graph of ethanol fermentation results of a fermentation substrate for finely pulverized rice straw, using each of wild-type yeast (NBRC1440 strain and TJ14 strain) and recombinant yeasts shown in Preparation Examples 2 to 4.

FIG. 2 shows a graph of ethanol fermentation results of a fermentation substrate for finely pulverized rice straw, using each of wild-type yeast (NBRC1440 strain and TJ14 strain) and the recombinant yeasts shown in Preparation Examples 2 to 4. The vertical axis indicates the ethanol concentration (g/L) in a liquid fermentation, and the horizontal axis indicates the fermentation time (hours). The symbols in the graph are as follows: a white circle represents NBRC1440 strain; a black circle represents recombinant yeast of Preparation Example 2; a black triangle represents recombinant yeast of Preparation Example 3; a white rhombus represents TJ14 strain; and a black rhombus represents recombinant yeast of Preparation Example 4.

As shown in FIG. 2, it was seen that a higher ethanol concentration was achieved by using yeast (20 g wet weight/L) expressing a single enzyme on the cell surface without expressing a plurality of enzymes on the cell surface, than by using the wild-type yeast.

Example 3: Ethanol Fermentation of Multiple Types of Finely Pulverized Lignocellulosic Biomass Napier grass, turf grass on golf courses, *Albizia falcataria*, and cedarwood were finely pulverized according to Reference Example 1 to obtain fermentation substrates. The resultant respective fermentation substrates were saccharified and fermented according to Reference Example 5, using each of wild-type yeast (TJ14 strain) and the recombinant yeast shown in Preparation Example 4 (the yeast obtained by engineering TJ14 strain to express ferulic acid esterase (FaeA) on the cell surface). Each of the resultant fermentation substrates was fed in a concentration of 20 (w/v) % with respect to the liquid fermentation, and a commercially available cellulase preparation (C-Tec2) was used in an amount of 10% by weight with respect to the weight of the finely pulverized material. The yeast cell concentration was set to 20 g wet weight/L with respect to the liquid fermentation. The finely pulverized cedarwood was also fed at a fed concentration of 30%.

Figure 3:
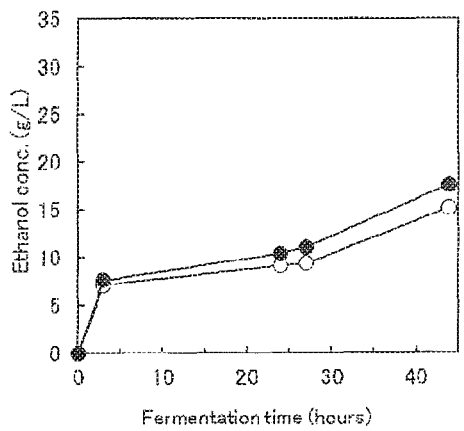
FIG. 3 shows graphs of ethanol fermentation results of fermentation substrates for finely pulverized napier grass (a), turf grass on golf courses (b), *Albizia falcataria* (c), and cedarwood (d and e) respectively, using each of wild-type yeast (TJ14 strain) and the recombinant yeast shown in Preparation Example 4.
Figure 3:
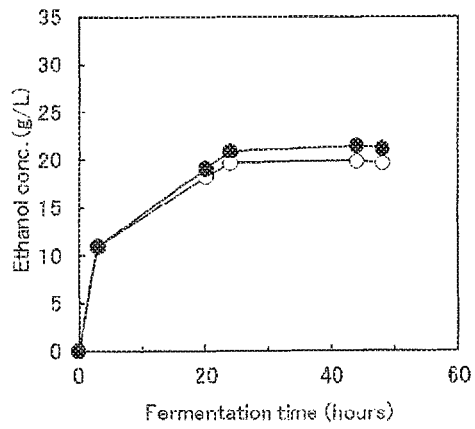
Figure 3:
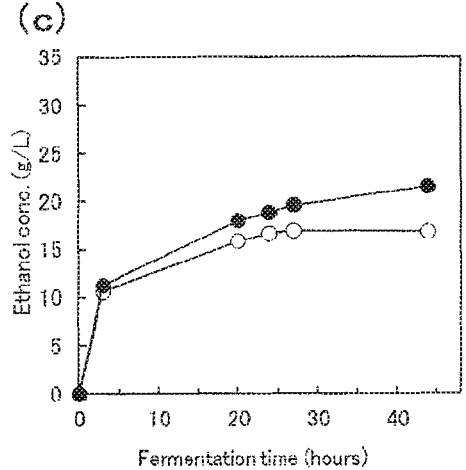
Figure 3:
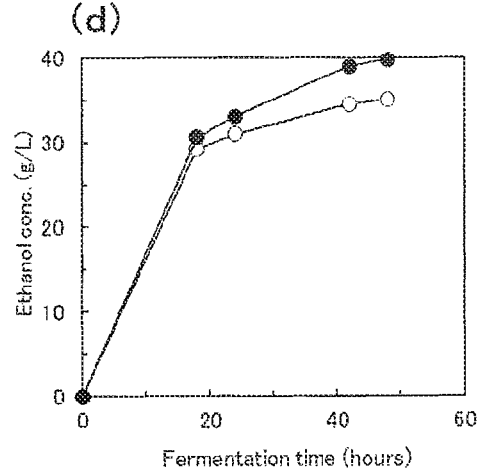
Figure 3:
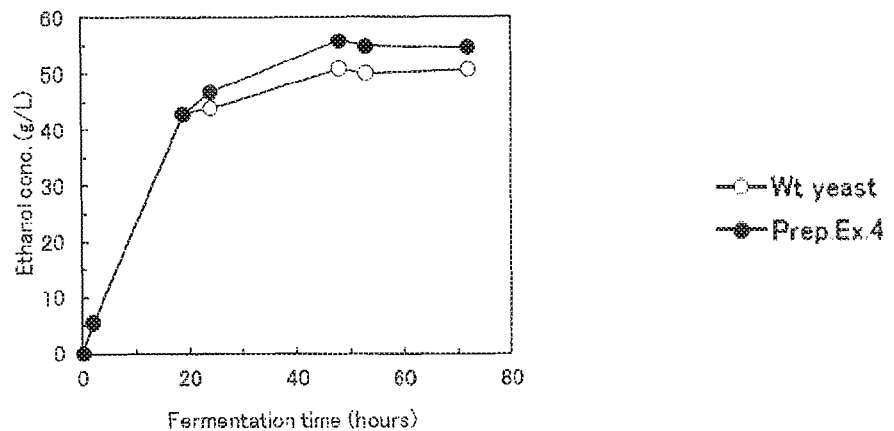

FIG. 3 shows graphs of ethanol fermentation results of fermentation substrates for finely pulverized napier grass (a), turf grass on golf courses (b), *Albizia falcataria* (c), and cedarwood (d and e) respectively, using each of wild-type yeast (TJ14 strain) and the recombinant yeast shown in Preparation Example 4. The vertical axis indicates the ethanol concentration (g/L) in a liquid fermentation, and the horizontal axis indicates the fermentation time (hours). The symbols in the graphs are as follows: a white circle represents TJ14 strain; and a black circle represents recombinant yeast of Preparation Example 4.

The FaeA-expressing yeast exhibited a higher ethanol concentration than that of the wild-type yeast (TJ14 strain) for any biomass used although the amount of ethanol produced varied depending on the sugar content in each target biomass (FIGS. 3(a) to 3(d)). When the concentration of cedarwood fed with respect to the liquid fermentation was increased from 20% to 30%, an even higher ethanol concentration was achieved as shown in FIG. 3(e). Also in this case, the FaeA-expressing yeast exhibited a higher ethanol concentration than that of the wild-type yeast (TJ14 strain).

Example 4: Ethanol Fermentation when Combining Hydrothermal Treatment and Finely Pulverizing Treatment Rice straw and bagasse were hydrothermally treated according to Reference Example 4 and then finely pulverized according to Reference Example 2 to obtain fermentation substrates. The resultant respective fermentation substrates were saccharified and fermented according to Reference Example 5, using each of wild-type yeast (TJ14 strain) and the recombinant yeast shown in Preparation Example 4 (the yeast obtained by engineering TJ14 strain to express ferulic acid esterase (FaeA) on the cell surface). Each of the resultant fermentation substrates was fed in a concentration of 20% with respect to the liquid fermentation, and a commercially available cellulase preparation (C-Tec2) was used in an amount of 10% by weight with respect to the weight of the finely pulverized material. The yeast cell concentration was set to 20 g wet weight/L with respect to the liquid fermentation.

Figure 4:
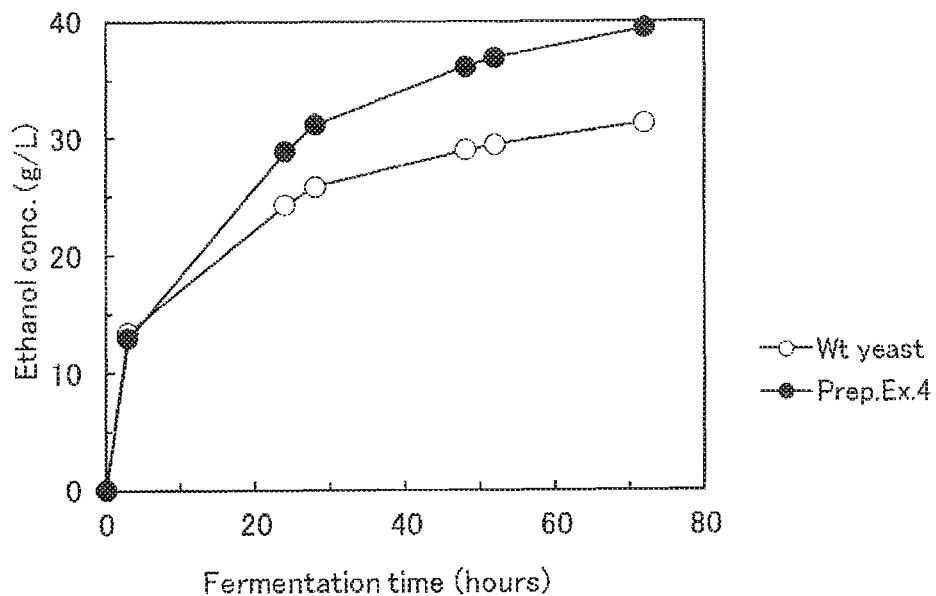
FIG. 4 shows graphs of ethanol fermentation results of fermentation substrates for hydrothermally treated and finely pulverized rice straw (a) and bagasse (b) respectively, using each of wild-type yeast (TJ14 strain) and the recombinant yeast shown in Preparation Example 4.
Figure 4:
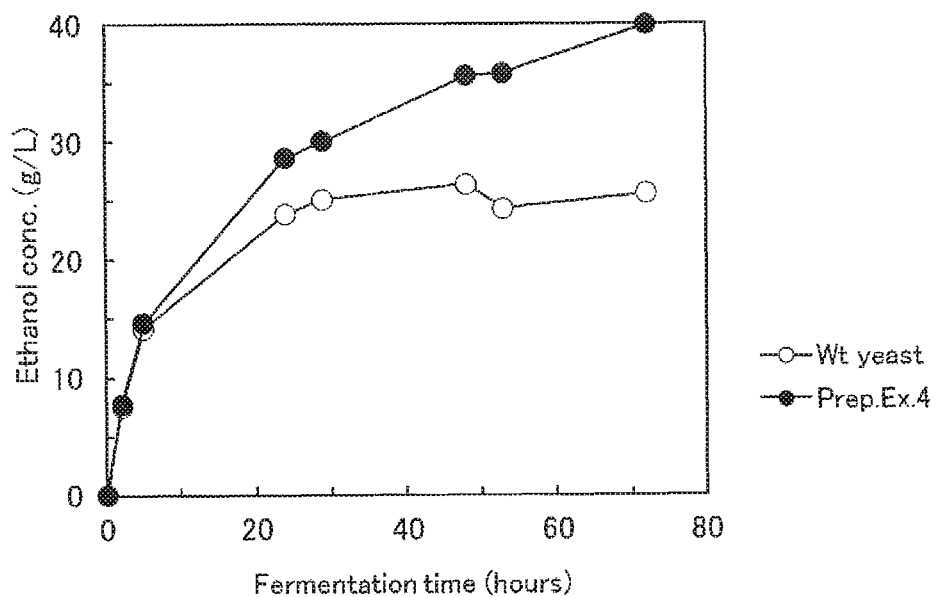

FIG. 4 shows graphs of ethanol fermentation results of fermentation substrates for hydrothermally treated and finely pulverized rice straw (a) and bagasse (b) respectively, using each of wild-type yeast (TJ14 strain) and the recombinant yeast shown in Preparation Example 4. The vertical axis indicates the ethanol concentration (g/L) in a liquid fermentation, and the horizontal axis indicates the fermentation time (hours). The symbols in the graphs are as follows: a white circle represents TJ14 strain; and a black circle represents recombinant yeast of Preparation Example 4.

As shown in FIG. 4(a), a difference in the ethanol production amount between the yeast displaying FaeA on the cell surface and the wild-type yeast was larger than that in the case where rice straw was finely pulverized (FIG. 2). Furthermore, also in the case of bagasse (FIG. 4(b)), a difference in the ethanol production amount was seen between the yeast displaying FaeA on the surface thereof and the wild-type yeast, as much or more than that of the rice straw. Accordingly, it was found that lignocellulosic biomass subjected to a combination of hydrothermal treatment and finely pulverizing treatment can be used as well for ethanol fermentation of microorganisms expressing an enzyme on the cell surfaces, and the amount of ethanol produced was significantly increased.

Example 5: Ethanol Fermentation by Yeast Having Xylose-Metabolizing Ability and Displaying Enzyme on Cell Surface Bagasse was hydrothermally treated according to Reference Example 4 and then finely pulverized according to Reference Example 2 to obtain a fermentation substrate. The resultant fermentation substrate was saccharified and fermented according to Reference Example 5, using each of the recombinant yeasts shown in Preparation Examples 5 and 6 (the yeast expressing X3, and the yeast expressing X3+displaying FaeA on the cell surface, respectively). The resultant fermentation substrate was fed in a concentration of 20 (w/v) % with respect to the liquid fermentation, and a commercially available cellulase preparation (C-Tec2) was used in an amount of 10% by weight with respect to the weight of the finely pulverized material. The yeast cell concentration was set to 20 g wet weight/L with respect to the liquid fermentation.

Figure 5:
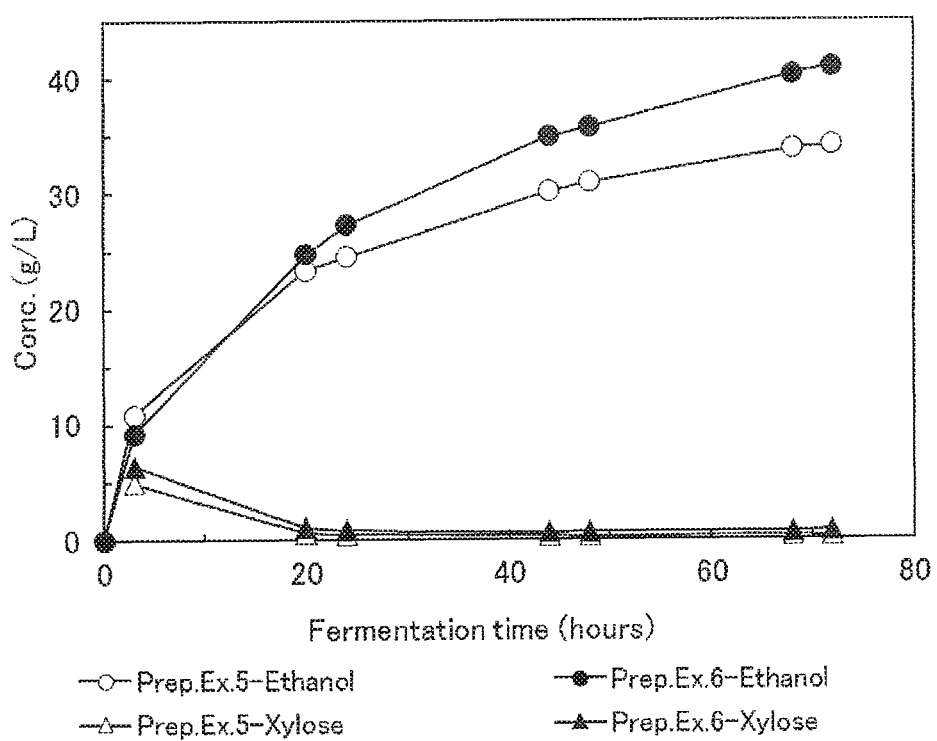
FIG. 5 shows a graph of ethanol fermentation results of hydrothermally treated and finely pulverized bagasse, using each of recombinant yeasts shown in Preparation Examples 5 and 6.

FIG. 5 shows a graph of ethanol fermentation results of hydrothermally treated and finely pulverized bagasse, using each of the recombinant yeasts shown in Preparation Examples 5 and 6. The vertical axis indicates the concentration of ethanol or xylose in a liquid fermentation (g/L), and the horizontal axis indicates the fermentation time (hours). The symbols in the graph are as follows: a white circle represents the amount of ethanol in a liquid fermentation in the case of recombinant yeast of Preparation Example 5 (yeast expressing X3); a black circle represents the amount of ethanol in a liquid fermentation in the case of recombinant yeast of Preparation Example 6 (yeast expressing X3+displaying FaeA on the cell surface); a white triangle represents the amount of xylose in a liquid fermentation in the case of recombinant yeast of Preparation Example 5; and a black triangle represents the amount of xylose in a liquid fermentation in the case of recombinant yeast of Preparation Example 6.

As shown in FIG. 5, both of the yeast expressing X3 and the yeast expressing X3+displaying FaeA on the cell surface utilized xylose. Furthermore, the yeast expressing X3+displaying FaeA on the cell surface realized an amount of ethanol produced higher than that of the yeast expressing X3 but not displaying FaeA on the cell surface.

Example 6: Influence of Particle Size of Finely Pulverized Biomass on Fermentation Efficiency 6-1: Measurement of Particle Size of Finely Pulverized Biomass Cedarwood was finely pulverized according to Reference Example 3 for a pulverization time period of 30 minutes, 45 minutes, and 60 minutes to obtain fermentation substrates. The particle size distributions of the resultant fermentation substrates were measured using a laser diffraction particle size analyzer (model: SALD-2300, manufactured by Shimadzu Corporation).

Figure 6:
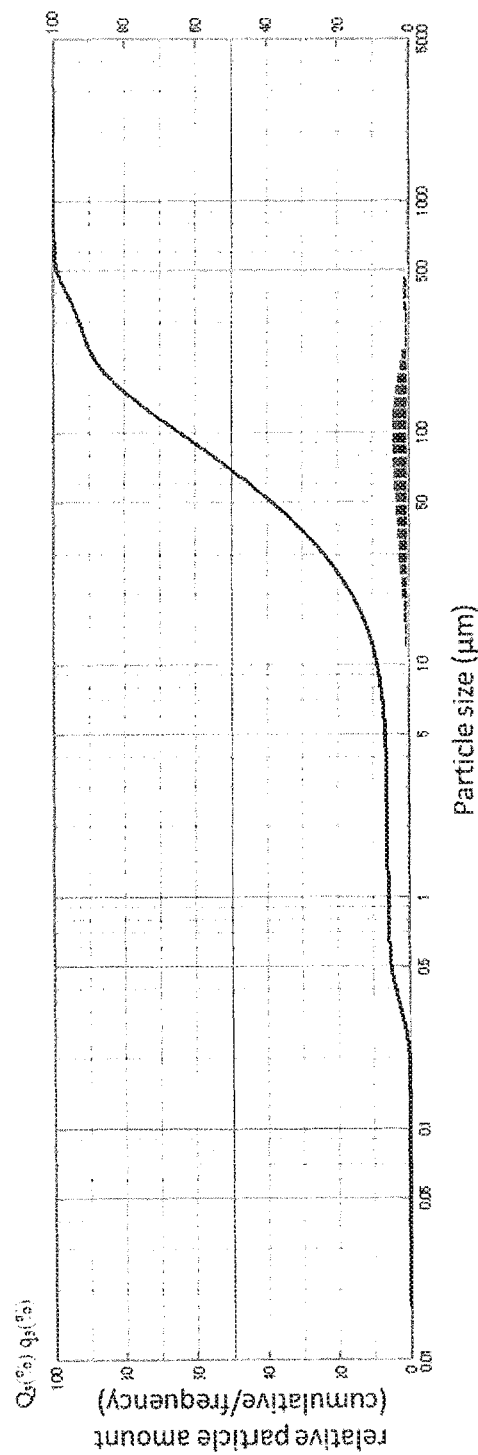
FIG. 6 shows particle size distributions when cedarwood cut into a length of 1 mm was treated with a mill (nano-mech REACTOR) for (a) 30 minutes, (b) 45 minutes, and (c) 60 minutes.
Figure 6:
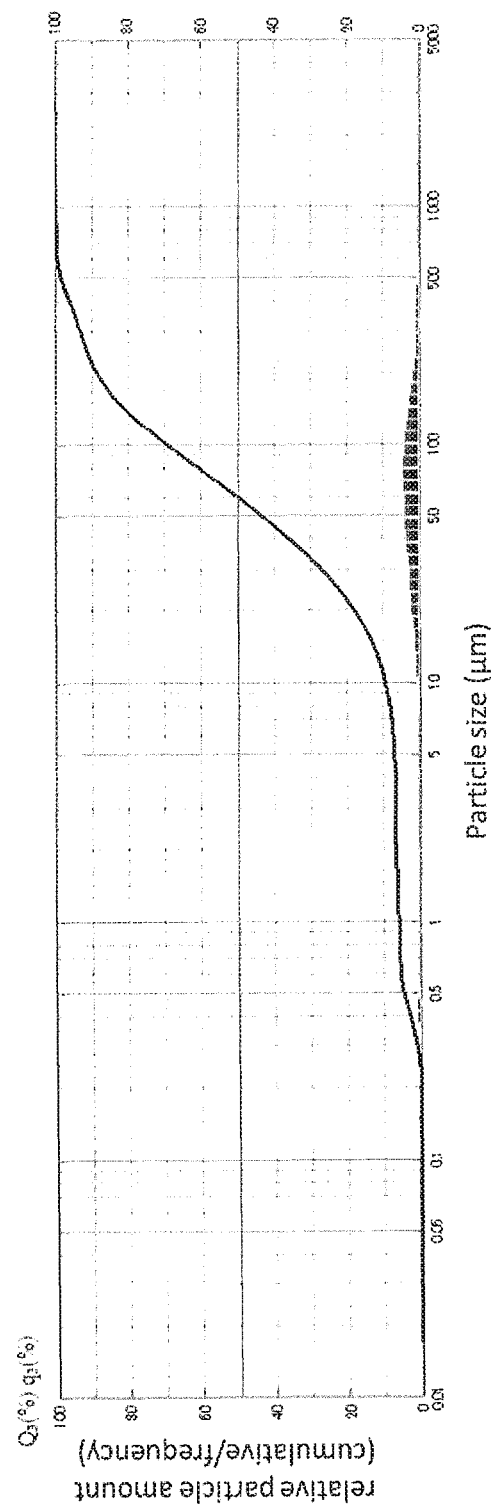
Figure 6:
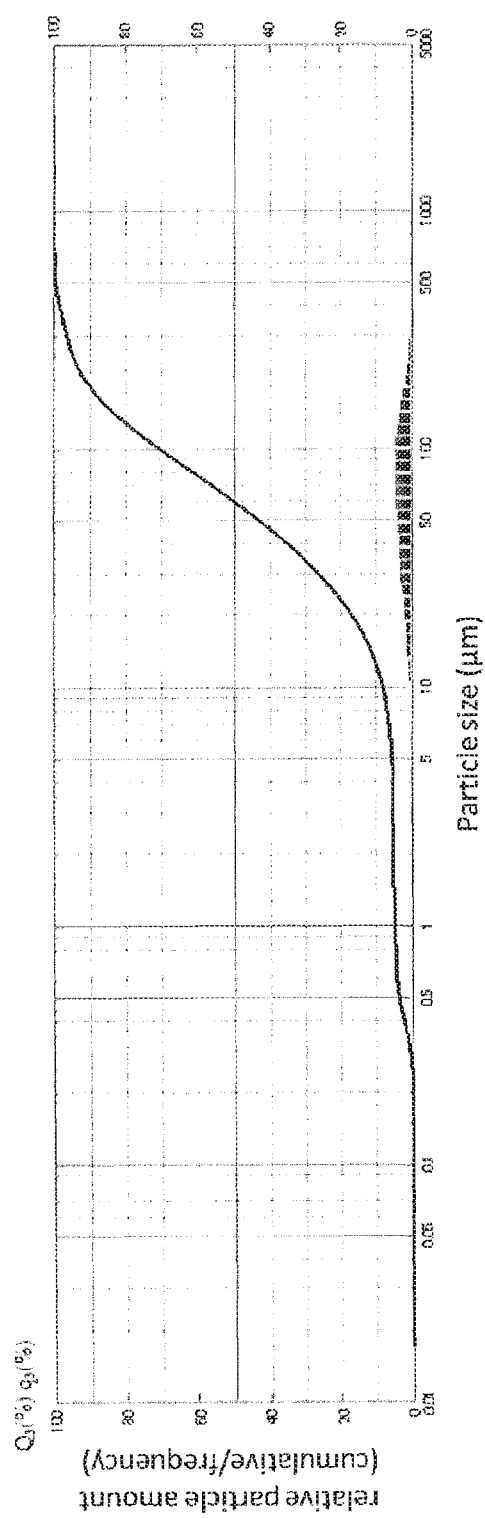

FIG. 6 shows particle size distributions when cedarwood cut to have a length of 1 mm was treated with a mill (nano-mech REACTOR) for (a) 30 minutes, (b) 45 minutes, and (c) 60 minutes. In all of FIGS. 6(a) to 6(c), the vertical axis indicates the relative particle amount (cumulative/frequency), and the horizontal axis indicates the particle size (μm). The half widths (d50) in the particle size distributions in (a), (b), and (c) were respectively 68.4 μm, 59.4 μm, and 59.6 μm.

When the pulverization time period was 30 minutes, 50% of the finely pulverized material had a particle size of 70 μm or less, and 90% had a particle size of 230 μm or less (FIG. 6(a)), when the pulverization time period was 45 minutes, 50% had a particle size of 60 μm or less, and 90% had a particle size of 220 μm or less (FIG. 6(b)), and, when the pulverization time period was 60 minutes, 50% had a particle size of 60 μm or less, and 90% had a particle size of 180 μm or less particle size (FIG. 6(c)). Among the pulverization time periods tested, any significant effect was not observed on the average particle size although differences were seen in the amount of particles with relatively large sizes (i.e., 300 to 500 μm). Even when the pulverization time is changed, the content of glucose in the finely pulverized biomass was hardly changed (Tables 1 and 2).

6-2: Fermentation by Yeast Displaying Ferulic Acid Esterase on Surface

The fermentation substrates (with pulverization time periods of 30 minutes, 45 minutes, and 60 minutes) obtained in 6-1 were saccharified and fermented according to Reference Example 5, using each of wild-type yeast (TJ14 strain) and the recombinant yeast shown in Preparation Example 4 (the yeast obtained by engineering TJ14 strain to express ferulic acid esterase (FaeA) on the cell surface) (only a fermentation substrate with a pulverization time period of 30 minutes was used for the TJ14 strain). Each of the resultant fermentation substrates was fed in a concentration of 20 (w/v) % with respect to the liquid fermentation, and a commercially available cellulase preparation (C-Tec2) was used in an amount of 10% by weight with respect to the weight of the finely pulverized material. The yeast cell concentration was set to 20 g wet weight/L with respect to the liquid fermentation.

Figure 7:
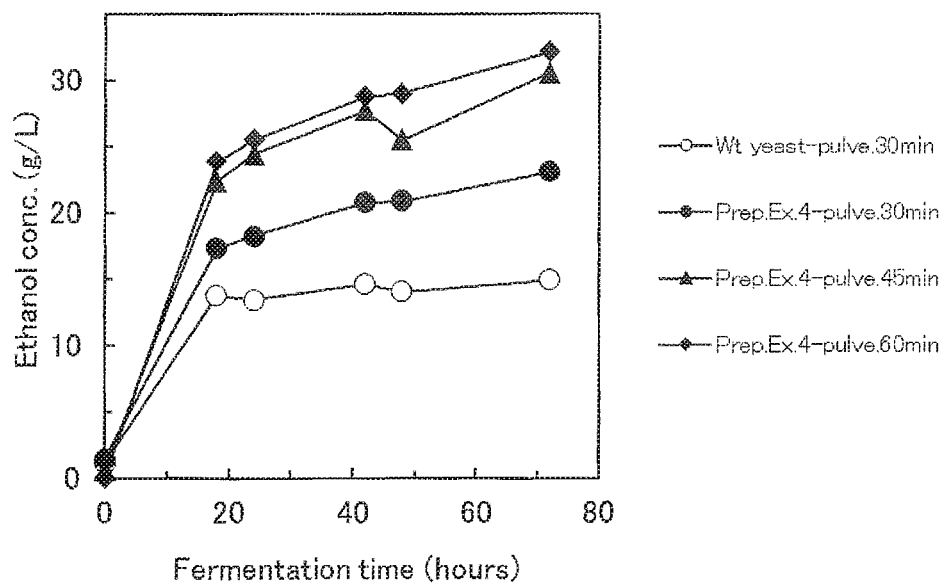
FIG. 7 shows a graph of ethanol fermentation results of fermentation substrates obtained with pulverization times of 30 minutes, 45 minutes, and 60 minutes, using wild-type yeast (TJ14 strain) and the recombinant yeast shown in Preparation Example 4.

FIG. 7 shows a graph of ethanol fermentation results of fermentation substrates obtained with pulverization time periods of 30 minutes, 45 minutes, and 60 minutes, using wild-type yeast (TJ14 strain) and the recombinant yeast shown in Preparation Example 4. The vertical axis indicates the ethanol concentration (g/L) in a liquid fermentation, and the horizontal axis indicates the fermentation time (hours). The symbols in the graph are as follows: a white circle represents a fermentation substrate with a pulverization time period of 30 minutes+TJ14 strain; a black circle represents a fermentation substrate with a pulverization time period of 30 minutes+recombinant yeast of Preparation Example 4; a black triangle represents a fermentation substrate with a pulverization time period of 45 minutes+recombinant yeast of Preparation Example 4; and a black rhombus represents a fermentation substrate with a pulverization time period of 60 minutes+recombinant yeast of Preparation Example 4.

As shown in FIG. 7, in the case of the wild-type yeast, the ethanol concentration was not increased (i.e., the enzyme saccharification rate was not increased) and remained substantially unchanged after 18 hours of the fermentation, whereas, in the case of the yeast displaying FaeA on the cell surface, the ethanol concentration was increased also after 18 hours of the fermentation. The reason for this seems to be that, in the case of the wild-type yeast, an enzyme that acts on saccharification of biomass is only the commercially available cellulase (CTec2) externally added, whereas, in the case of the yeast displaying FaeA on the cell surface, an enzyme on the cell surface facilitates saccharification of biomass up to the last stage of the fermentation. Accordingly, it seems that an externally added enzyme in a liquid fermentation is adsorbed, or prevented from being adsorbed, to biomass, so that it has a poor saccharification efficiency, however, an enzyme on the cell surface is kept in contact with finely pulverized biomass, so that it has a high saccharification efficiency.

Furthermore, a higher ethanol concentration (yield) was achieved with the yeast displaying FaeA on the cell surface, than with the wild-type yeast for any pulverization time period, and a comparison between the pulverization times showed that a longer pulverization time period achieved a better performance (Table 1).

TABLE 1

| Time Period of pulverising cedarwood | Yeast strain | Glucose content of pulverised cedarwood (wt %) | Glucose in fermentation system (g/L) | Theoretical ethanol conc. (g/L) | Ethanol conc. after 72 hrs of fermentation (g/L) | Yield (%) |
|---|---|---|---|---|---|---|
| 30 min | Wild type yeast | 39.9 | 79.9 | 40.7 | 14.9 | 36.6 |
|  | Preparation Example 4 | 39.9 | 79.9 | 40.7 | 23.0 | 56.5 |
| 45 min | Wild type yeast | 38.9 | 77.7 | 39.6 | 22.2 | 56.0 |
|  | Preparation Example 4 | 38.9 | 77.7 | 39.6 | 30.5 | 76.9 |
| 60 min | Wild type yeast | 39.7 | 79.5 | 40.5 | 25.3 | 62.4 |
|  | Preparation Example 4 | 39.7 | 79.5 | 40.5 | 32.1 | 79.2 |

6-3: Fermentation by Yeast Displaying Cellulase on Surface

Saccharification and fermentation were performed as in 6-2, except that wild-type yeast (NBRC1440 strain) and the recombinant yeast shown in Preparation Example 1 (NBRC1440 strain into which 2 copies of endoglucanase, 1 copy of cellobiohydrolase, and 1 copy off β-glucosidasewere introduced) were used.

Figure 8:
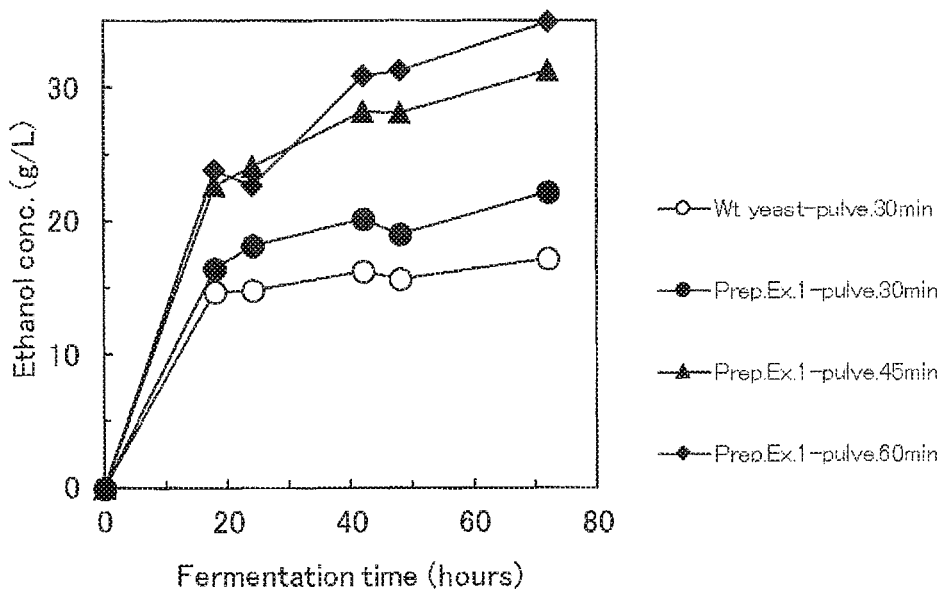
FIG. 8 shows a graph of ethanol fermentation results of fermentation substrates obtained with pulverization times of 30 minutes, 45 minutes, and 60 minutes, using wild-type yeast (NBRC1440 strain) and the recombinant yeast shown in Preparation Example 1.

FIG. 8 shows a graph of ethanol fermentation results of fermentation substrates obtained with pulverization time periods of 30 minutes, 45 minutes, and 60 minutes, using wild-type yeast (NBRC1440 strain) and the recombinant yeast shown in Preparation Example 1. The vertical axis indicates the ethanol concentration (g/L) in a liquid fermentation, and the horizontal axis indicates the fermentation time (hours). The symbols in the graph are as follows: a white circle represents a fermentation substrate with a pulverization time period of 30 minutes+wild-type yeast; a black circle represents a fermentation substrate with a pulverization time period of 30 minutes+recombinant yeast of Preparation Example 1; a black triangle represents a fermentation substrate with a pulverization time period of 45 minutes+recombinant yeast of Preparation Example 1; and a black rhombus represents a fermentation substrate with a pulverization time period of 60 minutes+recombinant yeast of Preparation Example 1.

As in the case of the recombinant yeast of Preparation Example 4 (the yeast displaying FaeA on the surface thereon, a higher ethanol concentration (yield) was achieved with the recombinant yeast of Preparation Example 1 (NBRC1440 strain into which 2 copies of endoglucanase, 1 copy of cellobiohydrolase, and 1 copy of β-glucosidase were introduced), than with the wild-type yeast, for any pulverization time period, and a comparison between the pulverization time periods showed that a longer pulverization time period achieved a better performance (Table 2 and FIG. 8).

TABLE 2

| Time Period of pulverising cedarwood | Yeast strain | Glucose content of pulverised cedarwood (wt %) | Glucose in fermentation system (g/L) | Theoretical ethanol conc. (g/L) | Ethanol conc. after 72 hrs of fermentation (g/L) | Yield (%) |
|---|---|---|---|---|---|---|
| 30 min | Wild type yeast | 39.9 | 79.9 | 40.7 | 17.2 | 42.2 |
|  | Preparation Example 1 | 39.9 | 79.9 | 40.7 | 22.2 | 54.5 |
| 45 min | Wild type yeast | 38.9 | 77.7 | 39.6 | 27.2 | 68.6 |
|  | Preparation Example 1 | 38.9 | 77.7 | 39.6 | 31.2 | 78.7 |
| 60 min | Wild type yeast | 39.7 | 79.5 | 40.5 | 28.0 | 69.1 |
|  | Preparation Example 1 | 39.7 | 79.5 | 40.5 | 34.9 | 86.1 |

Example 7: Influence of Orientation of Substrate-Binding Domain of Enzyme Displayed on Cell Surface, on Ethanol Fermentation of Finely Pulverized Biomass 7-1: Surface Display of Cellobiohydrolase I Bagasse was hydrothermally treated according to Reference Example 4 and then finely pulverized according to Reference Example 2 to obtain a fermentation substrate. The resultant fermentation substrate was saccharified and fermented according to Reference Example 5, using each of wild-type yeast (TJ14 strain) and the recombinant yeasts shown in Preparation Examples 7 and 8 ("CBHI-AG" obtained by engineering yeast to display the N-terminal side of cellobiohydrolase I (CBHI) on the surface thereof and "TIR-CBHI" obtained by engineering yeast to display the C-terminal side of cellobiohydrolase I (CBHI) on the surface thereof respectively). *Phanerochaete chrysosporium*-derived CBHI has a cellulose-binding domain (CBD) in the C-terminal side, and, thus, yeast displaying the N-terminal side of CBHI on the cell surface is yeast on which CBD is oriented inward to the cell, and yeast displaying the C-terminal side of CBHI on the cell surface is yeast on which CBD is oriented outward from the cell. The resultant fermentation substrate was fed in a concentration of 20% by weight with respect to the liquid fermentation, and a commercially available cellulase preparation (C-Tec2) was used in an amount of 10 (w/v) % with respect to the weight of the finely pulverized material. The yeast cell concentration was set to 20 g wet weight/L with respect to the liquid fermentation.

Figure 9:
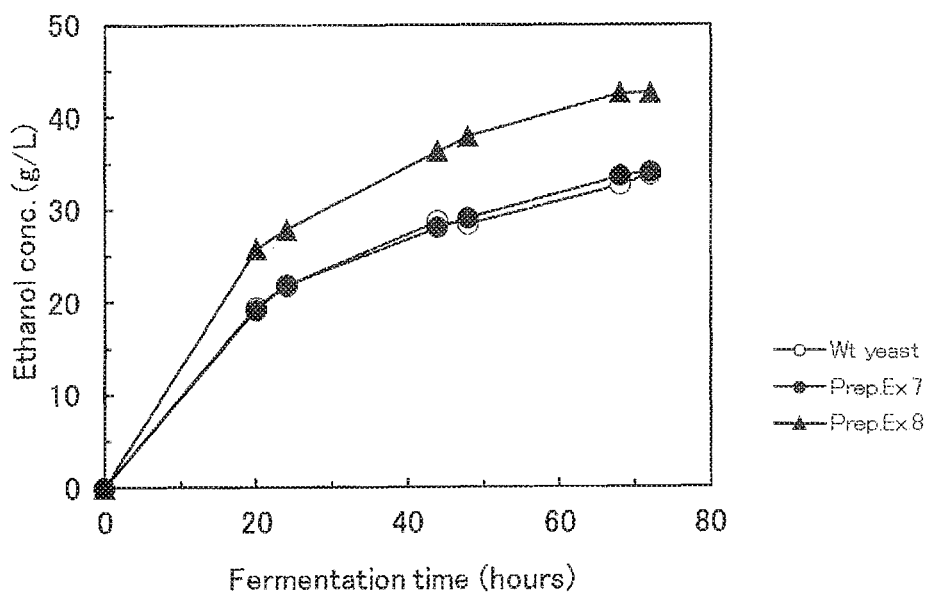
FIG. 9 shows a graph of ethanol fermentation results of hydrothermally treated and finely pulverized bagasse, using each of wild-type yeast (TJ14 strain) and recombinant yeasts shown in Preparation Examples 7 and 8.

FIG. 9 shows a graph of ethanol fermentation results of hydrothermally treated and finely pulverized bagasse, using each of wild-type yeast (TJ14 strain) and the recombinant yeasts shown in Preparation Examples 7 and 8. The vertical axis indicates the ethanol concentration (g/L) in a liquid fermentation, and the horizontal axis indicates the fermentation time (hours). The symbols in the graph are as follows: a white circle represents TJ14 strain; a black circle represents recombinant yeast of Preparation Example 7 ("CBHI-AG"); and a black triangle represents recombinant yeast of Preparation Example 8 ("TIR-CBHI").

As shown in FIG. 9, using the CBD of CBHI oriented inward into the cell ("CBHI-AG"), an ethanol concentration higher than that of the wild-type yeast was not achieved, but, using the CBD oriented outward ("TIR-CBHI"), an ethanol concentration higher than that of the wild-type yeast was achieved.

7-2: Surface Display of Endoglucanase I

Saccharification and fermentation were performed as in 7-1, except that wild-type yeast (TJ14 strain) and the recombinant yeasts shown in Preparation Examples 9 and 10 (the yeast displaying the N-terminal side of endoglucanase I (EGI) on the surface thereof and the yeast displaying the C-terminal side of endoglucanase I (EGI) on the surface thereof respectively) were used.

Figure 10:
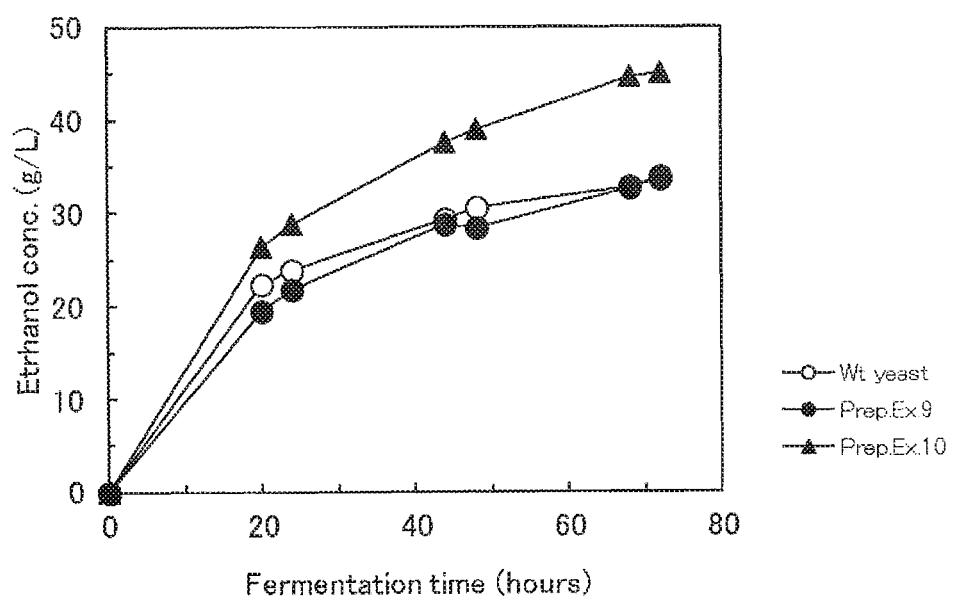
FIG. 10 shows a graph of ethanol fermentation results of hydrothermally treated and finely pulverized bagasse, using each of wild-type yeast (TJ14 strain) and recombinant yeasts shown in Preparation Examples 9 and 10.

FIG. 10 shows a graph of ethanol fermentation results of hydrothermally treated and finely pulverized bagasse, using each of wild-type yeast (TJ14 strain) and the recombinant yeasts shown in Preparation Examples 9 and 10. The vertical axis indicates the ethanol concentration (g/L) in a liquid fermentation, and the horizontal axis indicates the fermentation time (hours). The symbols in the graph are as follows: a white circle represents TJ14 strain; a black circle represents recombinant yeast of Preparation Example 9; and a black triangle represents recombinant yeast of Preparation Example 10.

As shown in FIG. 10, it was seen that a high ethanol concentration was achieved from finely pulverized biomass using the CBD oriented outward from the cell also for different enzymes such as endoglucanase I, having the CBD in the C-terminal side as in CBHI. That is to say, using the CBD of EGI oriented inward to the cell (Preparation Example 9), an ethanol concentration higher than that of the wild-type yeast was not achieved, however, using the CBD oriented outward (Preparation Example 10), an ethanol concentration higher than that of the wild-type yeast was achieved.

7-3: Surface Display of Ferulic Acid Esterase

Saccharification and fermentation were performed as in 7-1, except that wild-type yeast (TJ14 strain) and the recombinant yeast shown in Preparation Example 11 (the yeast displaying the C-terminus side of ferulic acid esterase on the cell surface) were used.

Figure 11:
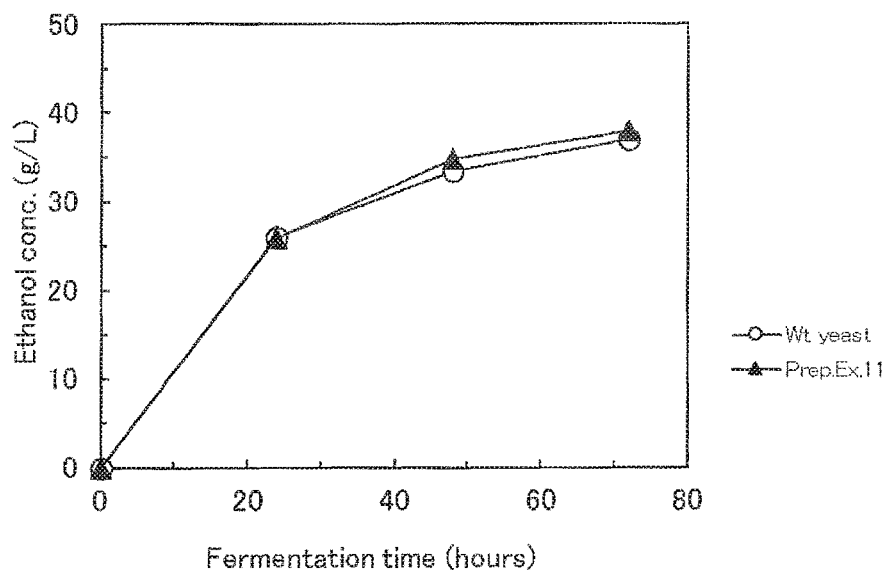
FIG. 11 shows a graph of ethanol fermentation results of hydrothermally treated and finely pulverized bagasse, using each of wild-type yeast (TJ14 strain) and recombinant yeast shown in Preparation Example 11.

FIG. 11 shows a graph of ethanol fermentation results of hydrothermally treated and finely pulverized bagasse, using each of wild-type yeast (TJ14 strain) and the recombinant yeast shown in Preparation Example 11. The vertical axis indicates the ethanol concentration (g/L) in a liquid fermentation, and the horizontal axis indicates the fermentation time (hours). The symbols in the graph are as follows: a white circle represents TJ14 strain; and a black triangle represents recombinant yeast of Preparation Example 11.

As shown in FIG. 11, when FaeA having the substrate-binding domain in the N-terminal side (in Preparation Examples 4 and 6, FaeA was displayed on the cell surface by linking the C-terminus of FaeA with the N-terminus of AG so that the substrate-binding domain of FaeA was oriented outward from the cell) was positioned by linking the N-terminus of FaeA with the C-terminus of TIR1 so that the substrate-binding domain of FaeA was oriented inward into the cell (Preparation Example 11), any significantly increased ethanol concentration was not observed compared with that of the wild-type yeast.

Accordingly, it seems that, in order to achieve an a high ethanol concentration from finely pulverized biomass, it is important to display an enzyme on the cell surface by linking it to an anchor protein such that its substrate-binding domain is oriented outward from the cell, regardless of whether it has the substrate-binding domain in the N-terminal side or the C-terminal side.

Reference Example 6: Lignocellulosic Biomass Finely Pulverizing Treatment 4

Rice husk was finely pulverized for 10 minutes using a nano-mech REACTOR (model: CM01, Simoloyer®, manufactured by Zoz GmbH, obtained from Techno-Eye Inc.).

Reference Example 7: Lignocellulosic Biomass Finely Pulverizing Treatment 5

Tapioca starch pulp was finely pulverized for 10 minutes using a nano-mech REACTOR (model: CM01, Simoloyer®, manufactured by Zoz GmbH, obtained from Techno-Eye Inc.).

Example 8: Simultaneous Saccharification and Fermentation of Finely Pulverized Rice Husk by Yeast Displaying Lignocellulose-Hydrolyzing Enzyme on Cell Surface In this example, the finely pulverized biomass (rice husk) of Reference Example 6 was saccharified and fermented using the recombinant yeast shown in Preparation Example 4, 8 or 10, or wild-type yeast TJ14 strain.

Saccharification and fermentation were performed as in Reference Example 5, except that the finely pulverized biomass (rice husk) was fed in a concentration of 20 (w/v) % with respect to the liquid fermentation, commercially available enzyme preparation was added in an amount of 8% by weight (C-Tec2: cellulase), 1% by weight (Neo-Spitase: liquefied α-amylase (manufactured by Nagase ChemteX Corporation)), and 1% by weight (Glucozyme: glucoamylase (manufactured by Nagase ChemteX Corporation)), with respect to the weight of the finely pulverized material, 1M citric acid buffer had a pH of 5.0, and the yeast cell concentration was set to 20 g wet weight/L with respect to the liquid fermentation.

Figure 12:
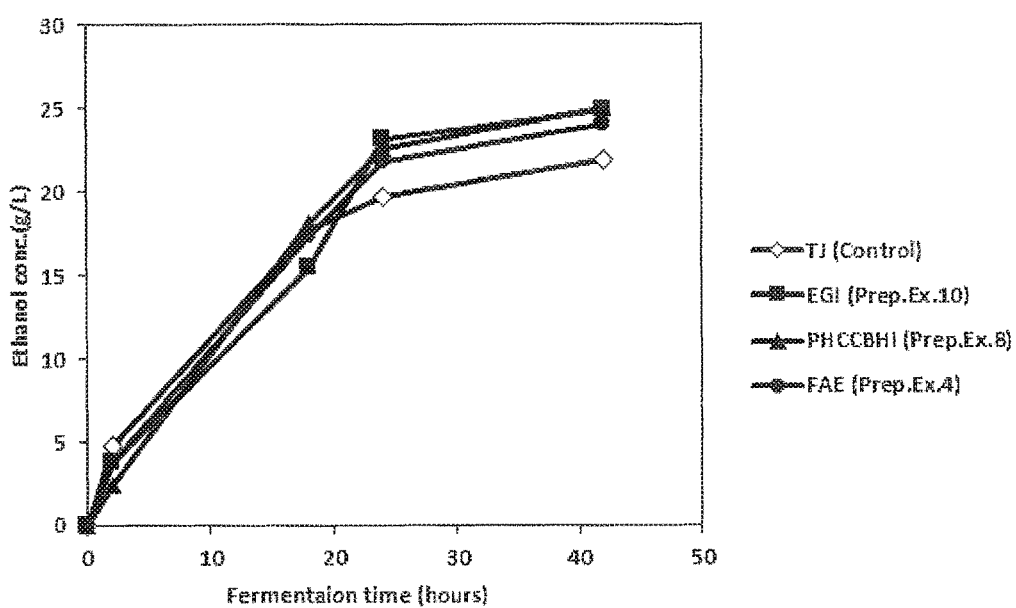
FIG. 12 shows a graph of ethanol fermentation results of finely pulverized rice husk, using each of wild-type yeast (TJ14 strain) and the recombinant yeasts shown in Preparation Examples 4, 8, and 10.

FIG. 12 shows a graph of ethanol fermentation results of finely pulverized rice husk, using each of wild-type yeast (TJ14 strain) and the recombinant yeasts shown in Preparation Examples 4, 8, and 10. The vertical axis indicates the ethanol concentration (g/L) in a liquid fermentation, and the horizontal axis indicates the fermentation time (hours). The symbols in the graph are as follows: a white rhombus represents TJ14 strain; a black circle represents Preparation Example 4; a black triangle represents Preparation Example 8; and a black square represents Preparation Example 10.

As shown in FIG. 12, even on the addition of enzymes (amylase and glucoamylase) for saccharifying starch contained in the starting material (rice husk), a higher ethanol concentration (yield) was achieved with the yeast displaying enzymes involved in hydrolysis of the lignocellulosic biomass on the cell surface, than with the wild-type yeast.

Preparation Example 12: Preparation of Yeast Displaying Amylase on Cell Surface As a first step, PCR amplification was performed using a primer HindIII-GAPp-Fw (Sequence ID No. 28) and a primer HindIII-GAPt-Rv (Sequence ID No. 29) with a plasmid pGA11 for displaying *Rhizopus oryzae*-derived glucoamylase on the cell surface (Murai et al., Applied and Environmental Microbiology 1997, Vol. 63, p. 1362-1366) as a template, so that a gene fragment containing a GAPDH (glyceraldehyde triphosphate dehydrogenase) promoter, a secretion signal sequence of a *Rhizopus oryzae*-derived glucoamylase gene, a *Rhizopus oryzae*-derived glucoamylase gene, the 3' half region of an α-agglutinin gene, and a GAPDH terminator was obtained. This gene fragment was inserted into a HindIII site of pRS405 (manufactured by Stratagene), so that a plasmid pRS405-GLA-AG for surface display of glucoamylase was formed.

Next, as a second step, the plasmid pRS405-GLA-AG obtained in the first step was cleaved with HpaI to have a linear form and introduced into NBRC1440/4UHWL (WO 2010/032762), and a strain having no leucine auxotrophy was selected.

Furthermore, as a third step, a plasmid pIU-G1uRAG-SBA for secretion of *Streptococcus bovis*-derived α-amylase and surface display of *Rhizopus oryzae*-derived glucoamylase (Yamada et al., Enzyme and Microbial Technology 2009, Vol. 44, p. 344-349) was cleaved with StuI to have a linear form and introduced into the strain selected in the second step, and a strain having no uracil auxotrophy was selected, which was taken as yeast of Additional Preparation Example 1 secreting 1 copy of α-amylase and displaying 2 copies of glucoamylase on the cell surface. The strain obtained in the third step was named [NBRC1440/pRS405-GLA-AG/pIU-GluRAG-SBA]. Since the substrate-binding domain of glucoamylase is positioned on the N-terminal side, the substrate-binding domain of glucoamylase was oriented outward from the cell for the surface displaying yeast obtained in this example.

The respective base sequences of the primers are as follows.

```
HindIII-GAPp-Fw:
                            (Sequence ID No. 28)
GGCAAGCTTACCAGTTCTCACACGGAACAC HindIII-GAPt-Rv:
                            (Sequence ID No. 29)
GGCAAGCTTTCAATCAATGAATCGAAAATGTC
```

Example 9: Simultaneous Saccharification and Fermentation of Finely Pulverized Tapioca by Yeast Displaying Amylase on Cell Surface In this example, the finely pulverized biomass (tapioca starch pulp) of Reference Example 7 was saccharified and fermented using the yeast of Preparation Example 12 or wild-type yeast NBRC1440 strain for control.

Yeast cells were cultured for 72 hours in a flask containing 100 mL of YPD liquid culture medium. After culturing for 72 hours, the yeast cell concentration in the YPD liquid culture medium was an amount corresponding to 20 g wet weight/L. Then, 7.5 mL of this yeast culture solution, 2.0 g of finely pulverized biomass, and 0.5 mL of 1M citric acid buffer (pH5.0) were put into a 50 mL plastic test tube (manufactured by Corning Incorporated) and then was incubated at 35° C. at a rotation rate of 35 rpm using a thermoblock rotator (SN-06BN, manufactured by Nissinrika).

The yeast cell concentration at the start of incubation in the 50 mL test tube was an amount corresponding to 15 g wet weight/L. During the incubation in the 50 mL test tube, no commercially available enzyme preparation such as cellulase or amylase was added. Furthermore, since the yeast culture solution obtained by the culturing of the YPD liquid in the flask contained a slight amount of ethanol, data was obtained during the time course by taking the ethanol concentration immediately after the start of incubation in the 50 mL test tube as zero.

Figure 13:
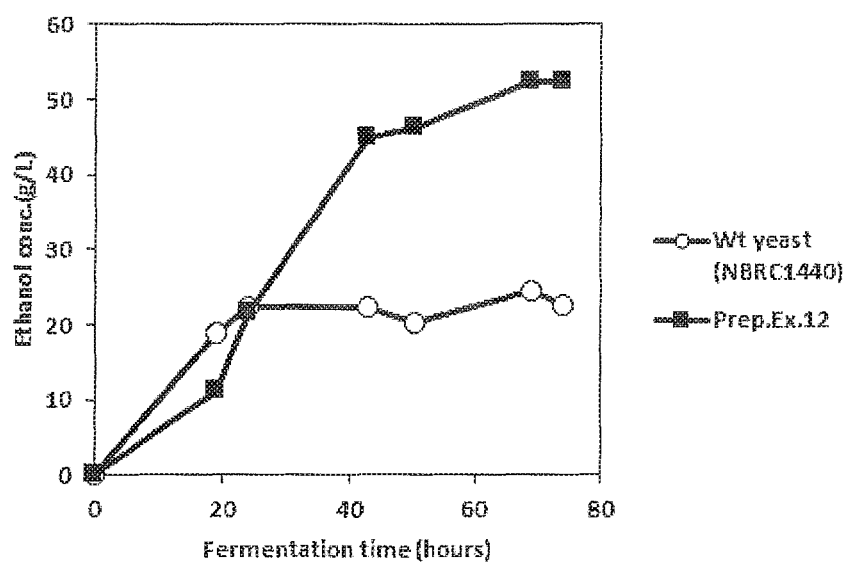
FIG. 13 shows a graph of ethanol fermentation results of finely pulverized tapioca starch pulp, using each of wild-type yeast (NBRC1440 strain) and recombinant yeast shown in Preparation Example 12.

FIG. 13 shows a graph of ethanol fermentation results of finely pulverized tapioca starch pulp, using each of wild-type yeast (NBRC1440 strain) and the recombinant yeast shown in Preparation Example 12. The vertical axis indicates the ethanol concentration (g/L) in a liquid fermentation, and the horizontal axis indicates the fermentation time (hours). The symbols in the graphs are as follows: a white circle represents wild-type yeast (NBRC1440 strain); and a black square represents Preparation Example 12.

As shown in FIG. 13, it was found that although the ethanol concentration was not increased after fermentation with the wild-type yeast after 24 hours of the fermentation, the ethanol concentration was significantly increased with the surface displaying yeast after 24 hours of the fermentation to achieve a higher ethanol concentration than with the wild-type yeast. It seems that although sugar in the finely pulverized biomass and to be used by the yeast for fermentation was completely consumed by the wild-type yeast within 24 hours of the fermentation, sugar to be used for fermentation was produced from the finely pulverized biomass with the glucoamylase displayed on the surface and the secreted α-amylase by the yeast of Preparation Example 12, making a contribution to production of ethanol even after 24 hours of the fermentation.

INDUSTRIAL APPLICABILITY

Use of lignocellulosic biomass particles obtained through finely pulverizing treatment or the like as a starting material of ethanol fermentation is advantageous in that the concentration of the starting material can be increased and that fermentation inhibiting substances can be reduced due to less history of being heated. Furthermore, the finely pulverizing treatment which can be used for preparation of lignocellulosic biomass particles is advantageous in many aspects in that no special chemical substance is used, that no waste is generated due to the treatment, and that a difference in the treatment effect resulting from the types of biomass is relatively small and the treatment can be applied to a wide range of biomass, for example.

---

The invention claimed is:

1. A method for producing ethanol, comprising:
culturing yeast transformed so as to display an enzyme on the cell surface in a medium containing particles of lignocellulosic biomass, thereby producing ethanol, wherein the enzyme is an enzyme involved in hydrolysis of the lignocellulosic biomass,
wherein the particles of the lignocellulosic biomass have an average particle size of 2 μm to 600 μm,
wherein the transformed yeast displays the enzyme on the cell surface so that a substrate-binding domain of the enzyme is oriented outward from the cell, and
wherein the yeast cell concentration at the start of fermentation is 2 g to 20 g wet weight/L.

2. The method of claim 1, wherein the lignocellulosic biomass further contains starch.

3. The method of claim 1, wherein the enzyme involved in hydrolysis of the lignocellulosic biomass is at least one enzyme selected from the group consisting of endoglucanase, cellobiohydrolase, β-glucosidase, ferulic acid esterase, β-galactosidase, pectinase, xylanase, xylosidase, acetylxylan esterase, arabinofuranosidase, swollenin, laccase, lignin peroxidase, glucoamylase, α-amylase, β-amylase, and pullulanase.

4. The method of claim 1, wherein the transformed yeast has xylose metabolizing ability.

5. The method of claim 1, further comprising finely pulverizing the lignocellulosic biomass.

6. The method of claim 1, further comprising hydrothermally treating the lignocellulosic biomass.

* * * * *

SEQUENCE LISTING

<160> NUMBER OF SEQ ID NOS: 29

<210> SEQ ID NO 1
<211> LENGTH: 28
<212> TYPE: DNA
<213> ORGANISM: Artificial Sequence
<220> FEATURE:
<223> OTHER INFORMATION: SS-XbaI-Fw

<400> SEQUENCE: 1
gctctagaat gcaactgttc aatttgcc                                      28

<210> SEQ ID NO 2
<211> LENGTH: 37
<212> TYPE: DNA
<213> ORGANISM: Artificial Sequence
<220> FEATURE:
<223> OTHER INFORMATION: AG-XbaI-Rv

<400> SEQUENCE: 2
gctctagatt tgattatgtt ctttctattt gaatgag                             37

<210> SEQ ID NO 3
<211> LENGTH: 114
<212> TYPE: DNA
<213> ORGANISM: Artificial Sequence
<220> FEATURE:
<223> OTHER INFORMATION: SalI-ssFaeA-Fw

<400> SEQUENCE: 3
acgcgtcgac atgcaactgt tcaatttgcc attgaaagtt tcattctttc tcgtcctctc    60
ttacttttct ttgctcgttt ctcagcaatc gctatggggc caatgcggtg gtac         114

<210> SEQ ID NO 4
<211> LENGTH: 38
<212> TYPE: DNA
<213> ORGANISM: Artificial Sequence
<220> FEATURE:
<223> OTHER INFORMATION: SalI-FaeA-Rv

<400> SEQUENCE: 4
acgcgtcgac gtggaataga gagaagaaac tccagatc                            38

<210> SEQ ID NO 5
<211> LENGTH: 36
<212> TYPE: DNA
<213> ORGANISM: Artificial Sequence
<220> FEATURE:
<223> OTHER INFORMATION: pAuR101-SphI-Fw

<400> SEQUENCE: 5
ctctgttgaa gcttggtaat acgactcact ataggg    36

<210> SEQ ID NO 6
<211> LENGTH: 35
<212> TYPE: DNA
<213> ORGANISM: Artificial Sequence
<220> FEATURE:
<223> OTHER INFORMATION: pAuR101-SphI-Rv

<400> SEQUENCE: 6
gagtcgacct gcaggaatta accctcacta aaggg    35

<210> SEQ ID NO 7
<211> LENGTH: 40
<212> TYPE: DNA
<213> ORGANISM: Artificial Sequence
<220> FEATURE:
<223> OTHER INFORMATION: IF-SS-PHCCBHI-Fw

<400> SEQUENCE: 7
tctttgctcg tttctgctaa tcacagaaca ctgaccagtc    40

<210> SEQ ID NO 8
<211> LENGTH: 36
<212> TYPE: DNA
<213> ORGANISM: Artificial Sequence
<220> FEATURE:
<223> OTHER INFORMATION: IF-AG-PHCCBHI-Rv

<400> SEQUENCE: 8
agagcttttg gcgctgtagc attgagagta gtatgg    36

<210> SEQ ID NO 9
<211> LENGTH: 36
<212> TYPE: DNA
<213> ORGANISM: Artificial Sequence
<220> FEATURE:
<223> OTHER INFORMATION: IF-101SphI-GAP-Fw

<400> SEQUENCE: 9
ctctgttgaa gcttgaccag ttctcacacg gaacac    36

<210> SEQ ID NO 10
<211> LENGTH: 42
<212> TYPE: DNA
<213> ORGANISM: Artificial Sequence
<220> FEATURE:
<223> OTHER INFORMATION: IF-101SacI-AG-Rv

<400> SEQUENCE: 10
cggccagtga attcgtttga ttatgttctt tctatttgaa tg    42

<210> SEQ ID NO 11
<211> LENGTH: 21
<212> TYPE: DNA
<213> ORGANISM: Artificial Sequence
<220> FEATURE:

<223> OTHER INFORMATION: AG-Fw

<400> SEQUENCE: 11
agcgccaaaa gctcttttat c                                              21

<210> SEQ ID NO 12
<211> LENGTH: 23
<212> TYPE: DNA
<213> ORGANISM: Artificial Sequence
<220> FEATURE:
<223> OTHER INFORMATION: SS-Rv

<400> SEQUENCE: 12 cttactttc tttgctcgtt tct                                             23

<210> SEQ ID NO 13
<211> LENGTH: 37
<212> TYPE: DNA
<213> ORGANISM: Artificial Sequence
<220> FEATURE:
<223> OTHER INFORMATION: IF-SS-TIR1-Fw

<400> SEQUENCE: 13
ttgctcgttt ctgctcaaac ccaagatcaa attaacg                              37

<210> SEQ ID NO 14
<211> LENGTH: 36
<212> TYPE: DNA
<213> ORGANISM: Artificial Sequence
<220> FEATURE:
<223> OTHER INFORMATION: IF-TIR1-PHCCBHI-Rv

<400> SEQUENCE: 14
cagtgttctg tgatttaaca acatagcggc agctgc                               36

<210> SEQ ID NO 15
<211> LENGTH: 26
<212> TYPE: DNA
<213> ORGANISM: Artificial Sequence
<220> FEATURE:
<223> OTHER INFORMATION: TAA-dAG-Fw

<400> SEQUENCE: 15
taaaacgggt actgtacagt tagtac                                          26

<210> SEQ ID NO 16
<211> LENGTH: 21
<212> TYPE: DNA
<213> ORGANISM: Artificial Sequence
<220> FEATURE:
<223> OTHER INFORMATION: PHCCBHI-dAG-Rv

<400> SEQUENCE: 16
gtagcattga gagtagtatg g                                               21

<210> SEQ ID NO 17
<211> LENGTH: 22
<212> TYPE: DNA
<213> ORGANISM: Artificial Sequence
<220> FEATURE:
<223> OTHER INFORMATION: PHCCBHI-Fw

<400> SEQUENCE: 17
aatcacagaa cactgaccag tc                                              22

<210> SEQ ID NO 18
<211> LENGTH: 28
<212> TYPE: DNA
<213> ORGANISM: Artificial Sequence
<220> FEATURE:
<223> OTHER INFORMATION: 101-StuI-Fw

<400> SEQUENCE: 18
cctcctatta ctgtcaaagt gttaccag                                28

<210> SEQ ID NO 19
<211> LENGTH: 22
<212> TYPE: DNA
<213> ORGANISM: Artificial Sequence
<220> FEATURE:
<223> OTHER INFORMATION: 101-StuI-Rv

<400> SEQUENCE: 19
cctgcggtca tctggaaagt ac                                      22

<210> SEQ ID NO 20
<211> LENGTH: 38
<212> TYPE: DNA
<213> ORGANISM: Artificial Sequence
<220> FEATURE:
<223> OTHER INFORMATION: IF-SS-EGI-Fw

<400> SEQUENCE: 20
tctttgctcg tttctgctca acaacctggt acctctac                     38

<210> SEQ ID NO 21
<211> LENGTH: 40
<212> TYPE: DNA
<213> ORGANISM: Artificial Sequence
<220> FEATURE:
<223> OTHER INFORMATION: IF-EGI-AG-Rv

<400> SEQUENCE: 21
agagcttttg gcgcttaagc attgagagta gtaatcattg                   40

<210> SEQ ID NO 22
<211> LENGTH: 36
<212> TYPE: DNA
<213> ORGANISM: Artificial Sequence
<220> FEATURE:
<223> OTHER INFORMATION: IF-TIR1-EGI-Rv

<400> SEQUENCE: 22
ggtaccaggt tgttgtaaca acatagcggc agctgc                       36

<210> SEQ ID NO 23
<211> LENGTH: 25
<212> TYPE: DNA
<213> ORGANISM: Artificial Sequence
<220> FEATURE:
<223> OTHER INFORMATION: EGI-dAG-Rv

<400> SEQUENCE: 23
taagcattga gagtagtaat cattg                                   25

<210> SEQ ID NO 24
<211> LENGTH: 20
<212> TYPE: DNA
<213> ORGANISM: Artificial Sequence
<220> FEATURE:
<223> OTHER INFORMATION: EGI-Fw

```
<400> SEQUENCE: 24
caacaacctg gtacctctac                                          20

<210> SEQ ID NO 25
<211> LENGTH: 36
<212> TYPE: DNA
<213> ORGANISM: Artificial Sequence
<220> FEATURE:
<223> OTHER INFORMATION: IF-TIR1-FaeA-Rv

<400> SEQUENCE: 25
ccatagcgat tgctgtaaca acatagcggc agctgc                        36

<210> SEQ ID NO 26
<211> LENGTH: 22
<212> TYPE: DNA
<213> ORGANISM: Artificial Sequence
<220> FEATURE:
<223> OTHER INFORMATION: FaeA-dAG-Rv

<400> SEQUENCE: 26
gtggaataga gagaagaaac tc                                       22

<210> SEQ ID NO 27
<211> LENGTH: 23
<212> TYPE: DNA
<213> ORGANISM: Artificial Sequence
<220> FEATURE:
<223> OTHER INFORMATION: FaeA-Fw

<400> SEQUENCE: 27
cagcaatcgc tatggggcca atg                                      23

<210> SEQ ID NO 28
<211> LENGTH: 30
<212> TYPE: DNA
<213> ORGANISM: Artificial Sequence
<220> FEATURE:
<223> OTHER INFORMATION: HindIII-GAPp-Fw

<400> SEQUENCE: 28
ggcaagctta ccagttctca cacggaacac                               30

<210> SEQ ID NO 29
<211> LENGTH: 32
<212> TYPE: DNA
<213> ORGANISM: Artificial Sequence
<220> FEATURE:
<223> OTHER INFORMATION: HindIII-GAPt-Rv

<400> SEQUENCE: 29
ggcaagcttt caatcaatga atcgaaaatg tc                            32
```